US008361977B2

(12) United States Patent
Baker et al.

(10) Patent No.: US 8,361,977 B2
(45) Date of Patent: Jan. 29, 2013

(54) COMPOSITIONS AND METHODS FOR MODULATION OF SMN2 SPLICING

(75) Inventors: Brenda F. Baker, Carlsbad, CA (US); Adrian R. Krainer, Huntington Station, NY (US); Yimin Hua, Jericho, NY (US)

(73) Assignee: Isis Pharmaceuticals, Inc., Carlsbad, CA (US)

(*) Notice: Subject to any disclaimer, the term of this patent is extended or adjusted under 35 U.S.C. 154(b) by 763 days.

(21) Appl. No.: 11/993,609

(22) PCT Filed: Jun. 23, 2006

(86) PCT No.: PCT/US2006/024469
§ 371 (c)(1),
(2), (4) Date: May 6, 2010

(87) PCT Pub. No.: WO2007/002390
PCT Pub. Date: Jan. 4, 2007

(65) Prior Publication Data
US 2010/0216238 A1 Aug. 26, 2010

Related U.S. Application Data

(60) Provisional application No. 60/693,542, filed on Jun. 23, 2005.

(51) Int. Cl.
C07H 21/02 (2006.01)
C07H 21/04 (2006.01)
A61K 31/70 (2006.01)
A61K 48/00 (2006.01)
C12Q 1/68 (2006.01)
C12N 5/00 (2006.01)

(52) U.S. Cl. .................... 514/44 A; 536/23.1; 536/24.1; 536/24.5

(58) Field of Classification Search .................. None
See application file for complete search history.

(56) References Cited

U.S. PATENT DOCUMENTS

| | | | |
|---|---|---|---|
| 5,176,996 A | 1/1993 | Hogan et al. | |
| 5,256,775 A | 10/1993 | Froehler | |
| 5,294,564 A | 3/1994 | Karapiperis et al. | |
| 5,627,274 A | 5/1997 | Kole et al. | |
| 5,801,154 A | 9/1998 | Baracchini et al. | |
| 6,172,216 B1 | 1/2001 | Bennett et al. | |
| 6,214,986 B1 | 4/2001 | Bennett et al. | |
| 6,376,508 B1 | 4/2002 | Li et al. | |
| 6,582,908 B2 | 6/2003 | Fodor et al. | |
| 6,753,423 B1 | 6/2004 | Cook et al. | |
| 6,770,633 B1 | 8/2004 | Robbins et al. | |
| 6,962,906 B2 | 11/2005 | Efimov et al. | |
| 7,034,009 B2 | 4/2006 | Pavco et al. | |
| 7,053,207 B2 | 5/2006 | Wengel | |
| 7,838,657 B2 * | 11/2010 | Singh et al. ................. 536/24.5 |
| 2001/0053519 A1 | 12/2001 | Fodor et al. | |
| 2003/0228597 A1 | 12/2003 | Cowsert et al. | |
| 2007/0031844 A1 | 2/2007 | Khvorova et al. | |
| 2007/0292408 A1 | 12/2007 | Singh et al. | |
| 2007/0299021 A1 | 12/2007 | Dunckley et al. | |
| 2008/0045456 A1 | 2/2008 | Greenway et al. | |
| 2012/0149757 A1 | 6/2012 | Krainer et al. | |
| 2012/0190728 A1 | 7/2012 | Bennett et al. | |

FOREIGN PATENT DOCUMENTS

| | | |
|---|---|---|
| WO | WO 94/26887 | 11/1994 |
| WO | WO 95/22980 | 8/1995 |
| WO | WO 01/09311 | 2/2001 |
| WO | WO 02/38738 | 5/2002 |
| WO | WO 2004/113867 | 12/2004 |
| WO | WO 2007/002390 | 1/2007 |

OTHER PUBLICATIONS

Batrakova et al., "Mechanism of Pluronic Effect on P-Glycoprotein Efflux System in Blood-Brain Barrier: Contributions of Energy Depletion and Membrane Fluidization" The Journal of Pharmacology and Experimental Therapeutics (2001) 299(2):483-493.
Branch et al., "A good antisense molecule is hard to find," TIBS (1998) 23:45-50.
Brichta et al., "Valproic acid increases the SMN2 protein level: a well-known drug as a potential therapy for spinal muscular atrophy" Human Molecular Genetics (2003) 12(19):2481-2489.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Crooke et al., "Basic Principles of Antisense Therapeutics" Antisense Research and Application (1998) Chapter 1:1-50.
Crooke, "Antisense strategies" Curr. Mol. Med. (2004) 4(5):465-487.
Dokka et al., "Novel non-endocyte delivery of antisense oligonucleotides" Advanced Drug Delivery Reviews (2000) 44:35-49.
Efimov et al., "Phosphono Peptide Nucleic Acids with a Constrained Hydroxyproline-Based Backbone" Nucleosides, Nucleotides & Nucleic Acids (2003) 22(5-8):593-599.
Forte et al., "Small interfering RNAs and Antisense Oligonucleotides for Treatment of Neurological Diseases" Current Drug Targets (2005) 6:21-29.
Heasman, "Morpholino Oligos: Making Sense of Antisense?" Developmental Biology (2002) 243:209-214.
Hofmann et al., "Htra2-beta1 stimulates an exonic splicing enhancer and can restor full-length SMN expression to survival motor neuron 2 (SMN2)" PNAS (2000) 97(17):9618-9623.
Ittig et al., "Nuclear antisense effects in cyclophilin A pre-mRNA splicing by oligonucleotides: a comparison of tricyclo-DNA with LNA" Nucleic Acids Research (2004) 32(10:346-353.
Jaeger et al., "Transport of Antisense Across the Blood-Brain Barrier" Methods in Molecular Medicine (2005) vol. 106: Antisense Therapeutics, Second Edition, I. Phillips (Ed.) Humana Press, Inc. Totowa, N.J., Cht. 12:237-251.

(Continued)

Primary Examiner — Sean McGarry
(74) Attorney, Agent, or Firm — Knobbe Martens

(57) ABSTRACT

Disclosed herein are compounds, compositions and methods for modulating splicing of SMN2 mRNA in a cell, tissue or animal. Also provided are uses of disclosed compounds and compositions in the manufacture of a medicament for treatment of diseases and disorders, including spinal muscular atrophy.

48 Claims, No Drawings

OTHER PUBLICATIONS

Kashima et al., "A negative element in SMN2 exon 7 inhibits splicing in spinal muscular atrophy." Nature Genetics (2003) 34(4):460-463.
Kole et al., "RNA modulation, repair and remodeling by splice switching oligonucleotides" Acta Biochimica Polonica (2004) 51(2):373-378.
Lorson et al., "A single nucleotide in the SMN gene regulates splicing and is responsible for spinal muscular atrophy" PNAS (1999) 96:6307-6311.
Lu et al., "Systemic delivery of antisense oligoribonucleotide restores dystrophin expression in body-wide skeletal muscles" PNAS (2005) 102(1):198-203.
Madocsai et al., "Correction of SMN2 Pre-mRNA Splicing by Antisense U7 Small Nuclear RNAs" Molecular Therapy (2005) 12(6):1013-1022.
New England Biolabs 1998/99 Catalog (cover page and pp. 121 and 284).
Rebuffat et al., "Gene delivery by a steroid-peptide nucleic acid conjugate" FASEB J. (2002) 19(11):1426-1428.
Reynolds et al., "Rational siRNA design for RNA interference" Nature Biotechnology (2004) 22(3):326-330.
Sanghvi et al., "Heterocyclic Base Modifications in Nucleic Acids and Their Applications in Antisense Oligonucleotides" Antisense Research and Applications (1993) pp. 273-288.
Sazani et al., "Therapeutic potential of antisense oligonucleotides as modulators of alternative splicing" The Journal of Clinical Investigation (2003) 112(4):481-486.
Singh et al., "In vivo selection reveals combinatorial controls that define a critical exon in the spinal muscular atrophy genes" RNA (2004) 10:1291-1305.
Singh et al., "An extended inhibitory context causes skipping of exon 7 of SMN2 in spinal muscular atrophy" Biochem. Biophys. Res. Comm. (2004) 315(2):381-388.
Veldink et al., "SMN genotypes producing less SMN protein increase susceptibility to and severity of sporadic ALS" Neurology (2005) 65(6):820-825.
Vinogradov et al., "Nanogels for Oligonucleotide Delivery to the Brain" Bioconjugate Chem. (2004) 15:50-60.
Wahlestedt et al., "Potent and nontoxic antisense oligonucleotides containined locked nucleic acids" PNAS (2000) 97(10):5633-5638.
International Search Report for application PCT/US10/30940 dated Jul. 13, 2010.
International Search Report for application PCT/US2010/39077 dated Aug. 17, 2010.
Categni et al., "Correction of disease-associated exon skipping by synthetic exon-specific activators" Nat. Struct. Biol. (2003) 10:120-125.
Dunckley et al., "Modification of splicing in the dystrophin gene in cultured mdx muscle cells by antisense oligoribonucleotides" Human Mol. Genetics (1998) 7(7):1083-1090.
Dunckley et al., "Modulation of Splicing in the DMD Gene by Antisense Oligoribonucleotides" Nucleosides & Nucleotides (1997) 16(7-9):1665-1668.
Friedman et al., "Correction of Aberrant Splicing of the Cystic Fibrosis Transmembrane Conductance Regulator (CFTR) Gene by Antisense Oligonucleotides" J. Biol. Chem. (1999) 274:36193-36199.
Hua et al., "Enhancement of SMN2 exon 7 inclusion by antisense oligonucleotides targeting the exon" PLOS Biology (2007) 5(4):E73.
Dominski et at, "Restoration of correct splicing in thalassemic pre-mRNA by antisense oligonucleotides" PNAS (1993) 90:8673-8677.
Kole, "Modification of pre-mRNA splicing by antisense oligonucleotides" Acta Biochimica Polonica (1997) 44(2):231-238.
Kurreck, "Antisense Technologies Improvement Through Novel Chemical Modifications" European Journal of Biochemistry (2003) 270(8):1628-1644.
Lacerra et al., "Restoration of hemoglobin A synthesis in erythroid cells from peripheral blood of thalassemic patients" PNAS (2000) 97(17):9591-9596.
LeFebvre et al., "The Role of the SMN Gene in Proximal Spinal Muscular Atrophy" Hum. Mol. Genet. (1998) 7(10):1531-1536.
Lim et al., "Modulation of Survival Motor Neuron Pre-mRNA Splicing by Inhibition of Alternative 3'Splice Site Pairing" J. Biol. Chem. (2001) 276(48):45476-45483.
Miyajima et al., "Identification of a Cis-Acting Element for the Regulation of SMN Exon 7 Splicing" J. Biol. Chem. (2002) 277(26):23271-23277.
Miyaso et al., "An Intronic Splicing Enhancer Element in Survival Motor Neuron (SMN) Pre-mRNA" J. Biol. Chem. (2003) 278(18):15825-15831.
Sierakowska et al., "Restoration of β-Globin Gene Expression in Mammalian Cells by Antisense Oligonucleotides That Modify the Aberrant Splicing Patierns of Thalassemic Pre-mRNAs" Nucleosides & Nucleotides (1997) 16(7-9):1173-1182.
Sierakowska et al., "Repair of thalassemic human β-globin mRNA in mammalian cells by antisense oligonucleotides" PNAS (1996) 93:12840-12844.
Singh et al., "Splicing of a critical exon of human Survival Motor Neuron is regulated by a unique silencer element located in the last intron" Molecular and Cellular Biology (2006) 26(4):1333-1346.
Skordis et al., "Bifunctional Antisense Oligonucleotides Provide a Trans-Acting Splicing Enhancer that Stimulated SMN2 Gene Expression in Patient Fibroblasts" PNAS (2003) 100(7):4114-4119.
Takeshima et al., "Modulation of in vitro splicing of the upstream intron by modifying an intra-exon sequence which is deleted from the dystrophin gene in dystrophin Kobe." J. Clin. Invest. (1995) 95(2):515-520.
Taylor et al., "Induction of endogenous Bcl-xS through the control of Bcl-x pre-mRNA splicing by antisense oligonucleotides" Nat. Biotechnol. (1999) 17:1097-1100.
Wang, "Antisense oligodeoxynucleotides selectively suppress expression of the mutant alpha 2(I) collagen allele in type IV osteogenesis imperfecta fibroblasts. A molecular approach to therapeutics of dominant negative disorders." J. Clin. Invest. (1996) 97(2):448-454.
Wilton et al., "Specific removal of the nonsense mutation from the mdx dystrophin mRNA using antisense oligonucleotides" Neuromuscul. Disord (1999) 9:330-338.
European Search Reprot for application EP 06773838 dated Aug. 11, 2010.
International Search Report for application PCT/US06/24469 dated Sep. 13, 2007.
Hua et al., "Antisense correction of SMN2 splicing in the CNS rescues necrosis in a type III SMA mouse model" Genes Dev. (2010) 24:1634-1644.

* cited by examiner

COMPOSITIONS AND METHODS FOR MODULATION OF SMN2 SPLICING

CROSS-REFERENCE TO RELATED APPLICATIONS

This Application is a national phase application of PCT application number PCT/US2006/024469, which claims priority to U.S. Provisional Patent Application Ser. No. 60/693,542, filed Jun. 23, 2005, which is incorporated by reference herein in its entirety.

INCORPORATION OF SEQUENCE LISTING

A copy of the sequence listing in both a paper form and a computer-readable form is provided herewith and incorporated by reference. The computer-readable form is provided on a 3.5" diskette containing the file named CORE0058WOSEQ.txt, which was created on Jun. 22, 2006.

BACKGROUND OF THE INVENTION

Newly synthesized eukaryotic mRNA molecules, also known as primary transcripts or pre-mRNA, made in the nucleus, are processed before or during transport to the cytoplasm for translation. Processing of the pre-mRNAs includes addition of a 5' methylated cap and an approximately 200-250 base poly(A) tail to the 3' end of the transcript.

The next step in mRNA processing is splicing of the pre-mRNA, which occurs in the maturation of 90-95% of mammalian mRNAs. Introns (or intervening sequences) are regions of a primary transcript (or the DNA encoding it) that are not included in the coding sequence of the mature mRNA. Exons are regions of a primary transcript that remain in the mature mRNA when it reaches the cytoplasm. The exons are spliced together to form the mature mRNA sequence. Splice junctions are also referred to as splice sites with the 5' side of the junction often called the "5' splice site," or "splice donor site" and the 3' side the "3' splice site" or "splice acceptor site." In splicing, the 3' end of an upstream exon is joined to the 5' end of the downstream exon. Thus the unspliced RNA (or pre-mRNA) has an exon/intron junction at the 5' end of an intron and an intron/exon junction at the 3' end of an intron. After the intron is removed, the exons are contiguous at what is sometimes referred to as the exon/exon junction or boundary in the mature mRNA. Cryptic splice sites are those which are less often used but may be used when the usual splice site is blocked or unavailable. Alternative splicing, defined as the splicing together of different combinations of exons, often results in multiple mRNA transcripts from a single gene.

Up to 50% of human genetic diseases resulting from a point mutation are caused by aberrant splicing. Such point mutations can either disrupt a current splice site or create a new splice site, resulting in mRNA transcripts comprised of a different combination of exons or with deletions in exons. Point mutations also can result in activation of a cryptic splice site or disrupt regulatory cis elements (i.e. splicing enhancers or silencers) (Cartegni et al., Nat. Rev. Genet., 2002, 3, 285-298; Drawczak et al., Hum. Genet., 1992, 90, 41-54).

Antisense oligonucleotides have been used to target mutations that lead to aberrant splicing in several genetic diseases in order to redirect splicing to give a desired splice product (Kole, Acta Biochimica Polonica, 1997, 44, 231-238). Such diseases include β-thalassemia (Dominski and Kole, Proc. Natl. Acad. Sci. USA, 1993, 90, 8673-8677; Sierakowska et al., Nucleosides & Nucleotides, 1997, 16,1173-1182; Sierakowska et al., Proc. Nag Acad. Sci. USA, 1996, 93, 12840-44; Lacerra et al., Proc. Natl. Acad. Sci. USA, 2000, 97, 9591-9596); dystrophin Kobe (Takeshima et al., J. Clin. Invest., 1995, 95, 515-520); Duchenne muscular dystrophy (Dunckley et al. Nucleosides & Nucleotides, 1997, 16, 1665-1668; Dunckley et al. Human Mol. Genetics, 1998, 5, 1083-90); osteogenesis imperfecta (Wang and Marini, J. Clin Invest., 1996, 97, 448-454); and cystic fibrosis (Friedman et al., J. Biol. Chem., 1999, 274, 36193-36199).

Antisense compounds have also been used to alter the ratio of the long and short forms of Bcl-x pre-mRNA (U.S. Pat. Nos. 6,172,216; 6,214,986; Taylor et al., Nat. Biotechnol. 1999, 17, 1097-1100) or to force skipping of specific exons containing premature termination codons (Wilton et al., Neuromuscul. Disord., 1999, 9, 330-338). U.S. Pat. No. 5,627,274 and WO 94/26887 disclose compositions and methods for combating aberrant splicing in a pre-mRNA molecule containing a mutation using antisense oligonucleotides which do not activate RNAse H.

Proximal spinal muscular atrophy (SMA) is a genetic, neurodegenerative disorder characterized by the loss of spinal motor neurons. SMA is an autosomal recessive disease of early onset and is currently the leading cause of death among infants. The severity of SMA varies among patients and has thus been classified into three types. Type I SMA is the most severe form with onset at birth or within 6 months and typically results in death within 2 years. Children with type I SMA are unable to sit or walk. Type II SMA is the intermediate form and patients are able to sit, but cannot stand or walk. Patients with type III SMA, a chronic form of the disease, typically develop SMA after 18 months of age (Lefebvre et al., Hum. Mol. Genet., 1998, 7, 1531-1536).

SMA is caused by the loss of both copies of survival of motor neuron 1 (SMN1), a protein that is part of a multiprotein complex thought to be involved in snRNP biogenesis and recycling. A nearly identical gene, SMN2, exists in a duplicated region on chromosome 5q13. Although SMN1 and SMN2 have the potential to code for the same protein, SMN2 contains a translationally silent mutation at position +6 of exon 7, which results in inefficient inclusion of exon 7 in SMN2 transcripts. Thus, the predominant form of SMN2 is a truncated version, lacking exon 7, which is unstable and inactive (Cartegni and Drainer, Nat. Genet., 2002, 30, 377-384).

Chimeric peptide nucleic acid molecules designed to modulate splicing of SMN2 have been described (WO 02/38738; Cartegni and Drainer, Nat. Struct. Biol., 2003, 10, 120-125).

Antisense technology is an effective means for modulating the expression of one or more specific gene products, including alternative splice products, and is uniquely useful in a number of therapeutic, diagnostic, and research applications. The principle behind antisense technology is that an antisense compound, which hybridizes to a target nucleic acid, modulates gene expression activities such as transcription, splicing or translation through one of a number of antisense mechanisms. The sequence specificity of antisense compounds makes them extremely attractive as tools for target validation and gene functionalization, as well as therapeutics to selectively modulate the expression of genes involved in disease.

Disclosed herein are antisense compounds useful for modulating gene expression and associated pathways via antisense mechanisms, which may include antisense mechanisms based on target occupancy. Provided herein are antisense compounds targeting SMN2 for use in modulation of SMN2 splicing. One having skill in the art, once armed with this disclosure will be able, without undue experimentation, to identify, prepare and exploit antisense compounds for these uses.

SUMMARY OF THE INVENTION

The present invention is directed to antisense compounds targeted to and hybridizable with a nucleic acid molecule encoding SMN2. Provided are antisense compounds targeted to intron, 6, exon 7 or intron 7 of SMN2 which modulate splicing of SMN2 pre-mRNAs. In one embodiment, modulation of splicing results in an increase in exon 7 inclusion. In another embodiment, modulation of splicing results in a decrease in exon 7 inclusion. Contemplated and provided herein are antisense compounds 12 to 20 nucleotides in length targeted to intron 6, exon 7 or intron 7 of SMN2, wherein the compounds comprise 2"-O-methoxyethyl sugar modifications.

In one aspect of the invention, the antisense compounds are targeted to cis splicing regulatory elements. Regulatory elements include exonic splicing enhancers, exonic splicing silencers, intronic splicing enhancers and intronic splicing silencers. Exonic and intronic splicing silencers are preferred targets.

In one embodiment, the antisense compounds comprise at least an 8-nucleobase portion of one of the exemplary compounds provided herein.

Also provided are methods for modulating splicing of SMN2 mRNA in a cell, tissue or organ using one or more of the compounds of the invention. In one embodiment, modulation of splicing is exon inclusion. In another embodiment, modulation of splicing is exon skipping. In one aspect, the compound is targeted to an intronic splicing silencer element. In another aspect, the compound is targeted to an exonic splicing silencer element.

Further provided are antisense compounds 10 to 50, 12 to 30 or 12 to 20 nucleotides in length targeted to intron 6, exon 7 or intron 7 of SMN2 comprising 2'-O-methoxyethyl sugar modifications for use in therapy. Also provided are pharmaceutical compositions comprising one or more of the compounds of the invention. Use of an antisense oligonucleotide provided herein for the preparation of a medicament for modulating splicing of an SMN2 pre-mRNA is also provided. In one aspect, modulation of splicing results in an increase in exon 7 inclusion. Use of an antisense oligonucleotide provided herein for the preparation of a medicament for the treatment of spinal muscular atrophy is further provided.

DETAILED DESCRIPTION OF THE INVENTION

Antisense technology is an effective means for modulating the expression of one or more specific gene products and is uniquely useful in a number of therapeutic, diagnostic, and research applications. Provided herein are antisense compounds useful for modulating gene expression via antisense mechanisms of action, including antisense mechanisms based on target occupancy. In one aspect, the antisense compounds provided herein modulate splicing of a target gene. Such modulation includes promoting or inhibiting exon inclusion. Further provided herein are antisense compounds targeted to cis splicing regulatory elements present in pre-mRNA molecules, including exonic splicing enhancers, exonic splicing silencers, intronic splicing enhancers and intronic splicing silencers. Disruption of cis splicing regulatory elements is thought to alter splice site selection, which may lead to an alteration in the composition of splice products.

Processing of eukaryotic pre-mRNAs is a complex process that requires a multitude of signals and protein factors to achieve appropriate mRNA splicing. Exon definition by the spliceosome requires more than the canonical splicing signals which define intron-exon boundaries. One such additional signal is provided by cis-acting regulatory enhancer and silencer sequences. Exonic splicing enhancers (ESE), exonic splicing silencers (ESS), intronic splicing enhancers (ISE) and intron splicing silencers (ISS) have been identified which either repress or enhance usage of splice donor sites or splice acceptor sites, depending on their site and mode of action (Yeo et al. 2004, *Proc. Natl. Acad. Sci. U.S.A.* 101(44):15700-15705). Binding of specific proteins (trans factors) to these regulatory sequences directs the splicing process, either promoting or inhibiting usage of particular splice sites and thus modulating the ratio of splicing products (Scamborova et al. 2004, *Mol. Cell. Biol.* 24(5):1855-1869; Hovhannisyan and Carstens, 2005, *Mol. Cell. Biol.* 25(1):250-263; Minovitsky et al. 2005, *Nucleic Acids Res.* 33(2):714-724). Little is known about the trans factors that interact with intronic splicing elements; however, several studies have provided information on exonic splicing elements. For example, ESEs are known to be involved in both alternative and constitutive splicing by acting as binding sites for members of the SR protein family. SR proteins bind to splicing elements via their RNA-binding domain and promote splicing by recruiting spliceosomal components with protein-protein interactions mediated by their RS domain, which is comprised of several Arg-Ser dipeptides (Cartegni and Krainer, 2003, *Nat. Struct. Biol.* 10(2):120-125; Wang et al. 2005, *Nucleic Acids Res.* 33(16):5053-5062). ESEs have been found to be enriched in regions of exons that are close to splice sites, particularly 80 to 120 bases from the ends of splice acceptor sites (Wu et al. 2005, *Genomics* 86:329-336). Consensus sequences have been determined for four members of the SR protein family, SF2/ASF, SC35, SRp40 and SRp55 (Cartegni et al. 2003, *Nucleic Acids Res.* 31(13):3568-3571).

Although the trans factors that bind intronic splicing regulatory elements have not been extensively studied, SR proteins and heterogeneous ribonucleoproteins (hnRNPs) have both been suggested to interact with these elements (Yeo et al. 2004, *Proc. Natl. Acad. Sci. U.S.A.* 101(44):15700-15705). Two intronic splicing enhancer elements (ISEs) have been identified in SMN2, one in intron 6 and the other in intron 7 (Miyajima et al. 2002, *J. Biol. Chem.* 22:23271-23277). Gel, shift assays using the ISE in intron 7 showed formation of RNA-protein complexes, which suggests these trans proteins may be important for regulation of splicing (Miyaso et al. 2003, *J. Biol. Chem.* 278(18):15825-15831).

The role of SMN2 in diseases such as spinal muscular atrophy (SMA) makes it an important therapeutic target. SMA is a genetic disorder characterized by degenefation of spinal motor neurons. SMA is caused by the loss of both functional copies of SMN1. However, SMN2 has the potential to code for the same protein as SMN1 and thus overcome the genetic defect of SMA patients. SMN2 contains a translationally silent mutation (C→T) at position +6 of exon 7 (nucleotide 66 of SEQ ID NO: 1), which results in inefficient inclusion of exon 7 in SMN2 transcripts. Therefore, the predominant form of SMN2, one which lacks exon 7, is unstable and inactive. Thus, therapeutic compounds capable of modulating SMN2 splicing such that the percentage of SMN2 transcripts containing exon 7 is increased, would be useful for the treatment of SMA.

Overview

Disclosed herein are oligomeric compounds, including antisense oligonucleotides and other antisense compounds for use in modulating the expression of nucleic acid molecules encoding SMN2. This is accomplished by providing oligomeric compounds which hybridize with one or more target nucleic acid molecules encoding SMN2. As used herein, the terms "target nucleic acid" and "nucleic acid molecule encoding SMN2" have been used for convenience to encompass DNA encoding SMN2, RNA (including pre-mRNA and mRNA or portions thereof) transcribed from such DNA, and also cDNA derived from such RNA.

Provided herein are antisense compounds for use in modulation of SMN2 pre-mRNA splicing. In one embodiment, the disclosed antisense compounds are targeted to exon 7 of SMN2 such that SMN mRNA splicing is modulated. In another embodiment, the antisense compounds are targeted to intron 6 of SMN2. In another embodiment, the antisense compounds are targeted to intron 7 of SMN2. Modulation of splicing may result in exon 7 inclusion or exon 7 skipping.

Also provided are antisense compounds targeted to cis regulatory elements. In one embodiment, the regulatory element is in an exon. In another embodiment, the regulatory element is an in intron.

Modulation of Splicing

As used herein, modulation of splicing refers to altering the processing of a pre-mRNA transcript such that the spliced mRNA molecule contains either a different combination of exons as a result of exon skipping or exon inclusion, a deletion in one or more exons, or additional sequence not normally found in the spliced mRNA (e.g., intron sequence). In the context of the present invention, modulation of splicing refers to altering splicing of SMN2 pre-mRNA to achieve exon skipping or exon inclusion. In one embodiment, exon skipping results in an SMN2 mRNA transcript lacking exon 7 and exon inclusion results in an SMN2 mRNA transcript containing exon 7.

As used herein, alternative splicing is defined as the splicing together of different combinations of exons, which may result in multiple mRNA transcripts from a single gene. In the context of the present invention, an SMN2 mRNA transcript containing exon 7 and an SMN2 mRNA transcript lacking exon 7 are two products of alternative splicing.

Compounds

The term "oligomeric compound" refers to a polymeric structure capable of hybridizing to a region of a nucleic acid molecule. This term includes oligonucleotides, oligonucleosides, oligonucleotide analogs, oligonucleotide mimetics and chimeric combinations of these. An "antisense compound" or "antisense oligomeric compound" refers to an oligomeric compound that is at least partially complementary to the region of a nucleic acid molecule to which it hybridizes and which modulates its expression. Consequently, while all antisense compounds can be said to be oligomeric compounds, not all oligomeric compounds are antisense compounds. An "antisense oligonucleotide" is an antisense compound that is a nucleic acid-based oligomer. An antisense oligonucleotide can be chemically modified. Nonlimiting examples of oligomeric compounds include primers, probes, antisense compounds, antisense oligonucleotides, external guide sequence (EGS) oligonucleotides, alternate splicers, and siRNAs. As such, these compounds can be introduced in the form of single-stranded, double-stranded, circular, branched or hairpins and can contain structural elements such as internal or terminal bulges or loops. Oligomeric double-stranded compounds can be two strands hybridized to form double-stranded compounds or a single strand with sufficient self complementarity to allow for hybridization and formation of a fully or partially double-stranded compound.

The oligomeric compounds in accordance with this invention may comprise a complementary oligomeric compound from about 10 to about 50 nucleobases (i.e. from about 10 to about 50 linked nucleosides). One having ordinary skill in the art will appreciate that this embodies antisense compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 nucleobases.

In one embodiment, the antisense compounds of the invention are 12 to 30 nucleobases. One having ordinary skill in the art will appreciate that this embodies antisense compounds of 12, 13, 14, 15, 16, 17, 18, 19, 20, 21, 22, 23, 24, 25, 26, 27, 28, 29 or 30 nucleobases.

In one embodiment, the antisense compounds of the invention are 12 to 20 nucleobases. One having ordinary skill in the art will appreciate that this embodies antisense compounds of 12, 13, 14, 15, 16, 17, 18, 19 or 20 nucleobases.

In one embodiment, the antisense compounds of the invention have antisense portions of 20 nucleobases.

In one embodiment, the antisense compounds of the invention have antisense portions of 18 nucleobases.

In one embodiment, the antisense compounds of the invention have antisense portions of 15 nucleobases.

In one embodiment, the antisense compounds of the invention have antisense portions of 12 nucleobases.

Antisense compounds 10-50 nucleobases in length comprising a stretch of at least eight (8) consecutive nucleobases selected from within the illustrative antisense compounds are considered to be suitable antisense compounds as well.

Compounds of the invention include oligonucleotide sequences that comprise at least the 8 consecutive nucleobases from the 5'-terminus of one of the illustrative antisense compounds (the remaining nucleobases being a consecutive stretch of nucleobases continuing upstream of the 5'-terminus of the antisense compound until the oligonucleotide contains about 10 to about 50 nucleobases). Other compounds are represented by oligonucleotide sequences that comprise at least the 8 consecutive nucleobases from the 3'-terminus of one of the illustrative antisense compounds (the remaining nucleobases being a consecutive stretch of nucleobases continuing downstream of the 3'-terminus of the antisense compound and continuing until the oligonucleotide contains about 10 to about 50 nucleobases). It is also understood that compounds may be represented by oligonucleotide sequences that comprise at least 8 consecutive nucleobases from an internal portion of the sequence of an illustrative compound, and may extend in either or both directions until the oligonucleotide contains about 10 to about 50 nucleobases. The compounds described herein are specifically hybridizable to the target nucleic acid.

One having skill in the art armed with the antisense compounds illustrated herein will be able, without undue experimentation, to identify further antisense compounds.

Hybridization

As used herein, "hybridization" means the pairing of complementary strands of antisense compounds to their target sequence. While not limited to a particular mechanism, the most common mechanism of pairing involves hydrogen bonding, which may be Watson-Crick, Hoogsteen or reversed Hoogsteen hydrogen bonding, between complementary nucleoside or nucleotide bases (nucleobases). For example, the natural base adenine is complementary to the natural nucleobases thymidine and uracil which pair through the formation of hydrogen bonds. The natural base guanine is complementary to the natural bases cytosine and 5-methyl cytosine. Hybridization can occur under varying circumstances.

An antisense compound is specifically hybridizable when there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

As used herein, "stringent hybridization conditions" or "stringent conditions" refers to conditions under which an antisense compound will hybridize to its target sequence, but to a minimal number of other sequences. Stringent conditions are sequence-dependent and will be different in different circumstances, and "stringent conditions" under which antisense compounds hybridize to a target sequence are determined by the nature and composition of the antisense compounds and the assays in which they are being investigated. Complementarity "Complementarity," as used herein, refers to the capacity for precise pairing between two nucleobases on either two oligomeric compound strands or an antisense compound with its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be a complementary position.

"Complementarity" can also be viewed in the context of an antisense compound and its target, rather than in a base by base manner. The antisense compound and the further DNA or RNA are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the antisense compound and a target nucleic acid. One skilled in the art recognizes that the inclusion of mismatches is possible without eliminating the activity of the antisense compound. The invention is therefore directed to those antisense compounds that may contain up to about 20% nucleotides that disrupt base pairing of the antisense compound to the target. Preferably the compounds contain no more than about 15%, more preferably not more than about 10%, most preferably not more than 5% or no mismatches. The remaining nucleotides do not disrupt hybridization (e.g., universal bases).

It is understood in the art that incorporation of nucleotide affinity modifications may allow for a greater number of mismatches compared to an unmodified compound. Similarly, certain oligonucleotide sequences may be more tolerant to mismatches than other oligonucleotide sequences. One of the skill in the art is capable of determining an appropriate number of mismatches between oligonucleotides, or between an oligonucleotide and a target nucleic acid, such as by determining melting temperature.

Identity

Antisense compounds, or a portion thereof, may have a defined percent identity to a SEQ ID NO, or a compound having a specific Isis number. As used herein, a sequence is identical to the sequence disclosed herein if it has the same nucleobase pairing ability. For example, a RNA which contains uracil in place of thymidine in the disclosed sequences of the instant invention would be considered identical as they both pair with adenine. This identity may be over the entire length of the oligomeric compound, or in a portion of the antisense compound (e.g., nucleobases 1-20 of a 27-mer may be compared to a 20-mer to determine percent identity of the oligomeric compound to the SEQ ID NO.) It is understood by those skilled in the art that an antisense compound need not have an identical sequence to those described herein to function similarly to the antisense compound described herein. Shortened versions of antisense compound taught herein, or non-identical versions of the antisense compound taught herein fall within the scope of the invention. Non-identical versions are those wherein each base does not have the same pairing activity as the antisense compounds disclosed herein. Bases do not have the same pairing activity by being shorter or having at least one abasic site. Alternatively, a non-identical version can include at least one base replaced with a different base with different pairing activity (e.g., G can be replaced by C, A, or T). Percent identity is calculated according to the number of bases that have identical base pairing corresponding to the SEQ ID NO or antisense compound to which it is being compared. The non-identical bases may be adjacent to each other, dispersed through out the oligonucleotide, or both.

For example, a 16-mer having the same sequence as nucleobases 2-17 of a 20-mer is 80% identical to the 20-mer. Alternatively, a 20-mer containing four nucleobases not identical to the 20-mer is also 80% identical to the 20-mer. A 14-mer having the same sequence as nucleobases 1-14 of an 18-mer is 78% identical to the 18-mer. Such calculations are well within the ability of those skilled in the art.

The percent identity is based on the percent of nucleobases in the original sequence present in a portion of the modified sequence. Therefore, a 30 nucleobase antisense compound comprising the full sequence of the complement of a 20 nucleobase active target segment would have a portion of 100% identity with the complement of the 20 nucleobase active target segment, while further comprising an additional 10 nucleobase portion. In the context of the invention, the complement of an active target segment may constitute a single portion. In a preferred embodiment, the oligonucleotides of the instant invention are at least about 80%, more preferably at least about 85%, even more preferably at least about 90%, most preferably at least 95% identical to at least a portion of the complement of the active target segments presented herein.

It is well known by those skilled in the art that it is possible to increase or decrease the length of an antisense compound and/or introduce mismatch bases without eliminating activity. For example, in Woolf et al. (Proc. Natl. Acad. Sci. USA 89:7305-7309, 1992, incorporated herein by reference), a series of ASOs 13-25 nucleobases in length were tested for their ability to induce cleavage of a target RNA. ASOs 25 nucleobases in length with 8 or 11 mismatch bases near the ends of the ASOs were able to direct specific cleavage of the target mRNA, albeit to a lesser extent than the ASOs that contained no mismatches. Similarly, target specific cleavage was achieved using a 13 nucleobase ASOs, including those with 1 or 3 mismatches. Maher and Dolnick (Nuc. Acid. Res. 16:3341-3358, 1988, incorporated herein by reference) tested a series of tandem 14 nucleobase ASOs, and a 28 and 42 nucleobase ASOs comprised of the sequence of two or three of the tandem ASOs, respectively, for their ability to arrest translation of human DHFR in a rabbit reticulocyte assay. Each of the three 14 nucleobase ASOs alone were able to inhibit translation, albeit at a more modest level than the 28 or 42 nucleobase ASOs. It is understood that antisense compounds of the instant invention can vary in length and percent complementarity to the target provided that they maintain the desired activity. Methods to determine desired activity are disclosed herein and well known to those skilled in the art.

Target Nucleic Acids

As used herein, "targeting" or "targeted to" refer to the process of designing an oligomeric compound such that the compound specifically hybridizes with a selected nucleic acid molecule.

"Targeting" an oligomeric compound to a particular target nucleic acid molecule can be a multistep process. The process usually begins with the identification of a target nucleic acid whose expression is to be modulated. As used herein, the terms "target nucleic acid" and "nucleic acid encoding SMN2" encompass DNA encoding $SMN^2$, RNA (including pre-mRNA and mRNA) transcribed from such DNA, and also cDNA derived from such RNA. For example, the target nucleic acid can be a cellular gene (or mRNA transcribed from the gene) whose expression is associated with a particular disorder or disease state, or a nucleic acid molecule from an infectious agent. As disclosed herein, the target nucleic acid encodes SMN2. In one preferred embodiment, the target nucleic acid is SMN2 pre-mRNA.

Target Regions, Segments, and Sites

The targeting process usually also includes determination of at least one target region, segment, or site within the target nucleic acid for the antisense interaction to occur such that the desired effect (e.g., modulation of splicing) will result. "Region" is defined as a portion of the target nucleic acid having at least one identifiable structure, function, or characteristic. Target regions may include an exon or an intron. Within regions of target nucleic acids are segments. "Segments" are defined as smaller or sub-portions of regions within a target nucleic acid. "Sites," as used in the present invention, are defined as unique nucleobase positions within a target nucleic acid.

Kits, Research Reagents and Diagnostics

The antisense compounds of the present invention can be utilized for diagnostics, and as research reagents and kits. Furthermore, antisense compounds, which are able to inhibit gene expression or modulate gene expression (e.g., modulation of splicing) with specificity, are often used by those of ordinary skill to elucidate the function of particular genes or to distinguish between functions of various members of a biological pathway. For use in kits and diagnostics, the antisense compounds of the present invention, either alone or in combination with other compounds or therapeutics, can be used as tools in differential and/or combinatorial analyses to elucidate expression patterns of a portion or the entire complement of genes expressed within cells and tissues. Methods of gene expression analysis are well known to those skilled in the art.

Therapeutics

Antisense compounds of the invention can be used to modulate the expression of SMN2 in an animal, such as a human. In one non-limiting embodiment, the methods comprise the step of administering to said animal in need of therapy for a disease or condition associated with SMN2 an effective amount of an antisense compound that modulates expression of SMN2 (e.g. modulates splicing of SMN2). A disease or condition associated with SMN2 includes, but is not limited to, spinal muscular atrophy. In one embodiment, the antisense compounds of the present invention effectively modulate splicing of SMN2, resulting in an increase in exon 7 inclusion. Antisense compounds of the present invention that effectively modulate expression of SMN2 RNA or protein products of expression are considered active antisense compounds.

For example, modulation of expression of SMN2 can be measured in a bodily fluid, which may or may not contain cells; tissue; or organ of the animal. Methods of obtaining samples for analysis, such as body fluids (e.g., sputum, serum), tissues (e.g., biopsy), or organs, and methods of preparation of the samples to allow for analysis are well known to those skilled in the art. Methods for analysis of RNA and protein levels are discussed above and are well known to those skilled in the art. The effects of treatment can be assessed by measuring biomarkers associated with the target gene expression in the aforementioned fluids, tissues or organs, collected from an animal contacted with one or more compounds of the invention, by routine clinical methods known in the art. These biomarkers include but are not limited to: liver transaminases, bilirubin, albumin, blood urea nitrogen, creatine and other markers of kidney and liver function; interleukins, tumor necrosis factors, intracellular adhesion molecules, C-reactive protein, chemokines, cytokines, and other markers of inflammation.

The antisense compounds of the present invention can be utilized in pharmaceutical compositions by adding an effective amount of a compound to a suitable pharmaceutically acceptable diluent or carrier. Acceptable carriers and diluents are well known to those skilled in the art. Selection of a diluent or carrier is based on a number of factors, including, but not limited to, the solubility of the compound and the route of administration. Such considerations are well understood by those skilled in the art. In one aspect, the antisense compounds of the present invention modulate splicing of SMN2. The compounds of the invention can also be used in the manufacture of a medicament for the treatment of diseases and disorders related to SMN2.

Methods whereby bodily fluids, organs or tissues are contacted with an effective amount of one or more of the antisense compounds or compositions of the invention are also contemplated. Bodily fluids, organs or tissues can be contacted with one or more of the compounds of the invention resulting in modulation of SMN2 expression in the cells of bodily fluids, organs or tissues. An effective amount can be determined by monitoring the modulatory effect of the antisense compound or compounds or compositions on target nucleic acids or their products by methods routine to the skilled artisan.

Thus, provided herein is the use of an isolated antisense compound targeted to SMN2 in the manufacture of a medicament for the treatment of a disease or disorder by means of the method described above. In one embodiment, the antisense compound is targeted to exon 7 of SMN2. In another embodiment, the antisense compound is targeted to intron 6 of SMN2. In yet another embodiment, the antisense compound is targeted to intron 7 of SMN2.

Chemical Modifications

As is known in the art, a nucleoside is a base-sugar combination. The base portion of the nucleoside is normally a heterocyclic base (sometimes referred to as a "nucleobase" or simply a "base"). The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. In forming oligonucleotides, the phosphate groups covalently link adjacent, nucleosides to one another to form a linear polymeric compound. Within oligonucleotides, the phosphate groups are commonly referred to as forming the internucleoside backbone of the oligonucleotide. The normal linkage or backbone of RNA and DNA is a 3' to 5' phosphodiester linkage. It is often preferable to include chemical modifications in oligonucleotides to alter their activity. Chemical modifications can alter oligonucleotide activity by, for example: increasing affinity of an antisense oligonucleotide for its target RNA, increasing nuclease resistance, and/or altering the pharmacokinetics of the oligonucleotide. The use of chemistries that increase the affinity of an oligonucleotide for its target can allow for the use of shorter oligonucleotide compounds.

The term "nucleobase" or "heterocyclic base moiety" as used herein, refers to the heterocyclic base portion of a nucleoside. In general, a nucleobase is any group that contains one or more atom or groups of atoms capable of hydrogen bonding to a base of another nucleic acid. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to the present invention. The terms modified nucleobase and nucleobase mimetic can overlap but generally a modified nucleobase refers to a nucleobase that is fairly similar in structure to the parent nucleobase, such as for example a 7-deaza purine, a 5-methyl cytosine, or a G-clamp, whereas a nucleobase mimetic would include more complicated structures, such as for example a tricyclic phenoxazine nucleobase mimetic. Methods for preparation of the above noted modified nucleobases are well known to those skilled in the art.

Antisense compounds of the present invention may also contain one or more nucleosides having modified sugar moieties. The furanosyl sugar ring of a nucleoside can be modified in a number of ways including, but not limited to, addition of a substituent group, bridging of two non-geminal ring atoms to form a bicyclic nucleic acid (BNA) and substitution of an atom or group such as —S—, —N(R)— or —C($R_1$)($R_2$) for the ring oxygen at the 4'-position. Modified sugar moieties are well known and can be used to alter, typically increase, the affinity of the antisense compound for its target and/or increase nuclease resistance. A representative list of preferred modified sugars includes but is not limited to bicyclic modified sugars (BNA's), including LNA and ENA (4'-(CH$_2$)$_2$— O-2' bridge); and substituted sugars, especially 2'-substituted sugars having a 2'-F, 2'-OCH$_2$ or a 2'-O(CH$_2$)$_2$—OCH$_3$ substituent group. Sugars can also be replaced with sugar mimetic groups among others. Methods for the preparations of modified sugars are well known to those skilled in the art.

The present invention includes internucleoside linking groups that link the nucleosides or otherwise modified monomer units together thereby forming an antisense compound. The two main classes of internucleoside linking groups are defined by the presence or absence of a phosphorus atom. Representative phosphorus containing internucleoside linkages include, but are not limited to, phosphodiesters, phosphotriesters, methylphosphonates, phosphoramidate, and phosphorothioates. Representative non-phosphorus containing internucleoside linking groups include, but are not limited to, methylenemethylimino (—CH$_2$—N(CH$_3$)—O—CH$_2$—), thiodiester (—O—C(O)—S—), thionocarbamate (—O—C(O)(NH)—S—); siloxane (—O—Si(H)$_2$—O—); and N,N$^1$-dimethylhydrazine (—CH$_2$—N(CH$_3$)—N(CH$_3$)—). Antisense compounds having non-phosphorus internucleoside linking groups are referred to as oligonucleosides. Modified internucleoside linkages, compared to natural phosphodiester linkages, can be used to alter, typically increase, nuclease resistance of the antisense compound. Internucleoside linkages having a chiral atom can be prepared racemic, chiral, or as a mixture. Representative chiral internucleoside linkages include, but are not limited to, alkylphosphonates and phosphorothioates. Methods of preparation of phosphorous-containing and non-phosphorous-containing linkages are well known to those skilled in the art.

As used herein the term "mimetic" refers to groups that are substituted for a sugar, a nucleobase, and/or internucleoside linkage. Generally, a mimetic is used in place of the sugar or sugar-iriternueleoside linkage combination, and the nucleobase is maintained for hybridization to a selected target. Representative examples of a sugar mimetic include, but are not limited to, cyclohexenyl or morpholino. Representative examples of a mimetic for a sugar-internucleoside linkage combination include, but are not limited to, peptide nucleic acids (PNA) and morpholino groups linked by uncharged achiral linkages. In some instances a mimetic is used in place of the nucleobase. Representative nucleobase mimetics are well known in the art and include, but are not limited to, tricyclic phenoxazine analogs and universal bases (Berger et al., Nuc Acid Res. 2000, 28:2911-14, incorporated herein by reference). Methods of synthesis of sugar, nucleoside and nucleobase mimetics are well known to those skilled in the art.

As used herein the term "nucleoside" includes, nucleosides, abasic nucleosides, modified nucleosides, and nucleosides having mimetic bases and/or sugar groups.

In the context of this invention, the term "oligonucleotide" refers to an oligomeric compound which is an oligomer or polymer of ribonucleic acid (RNA) or deoxyribonucleic acid (DNA). This term includes oligonucleotides composed of naturally- and non-naturally-occurring nucleobases, sugars and covalent internucleoside linkages, possibly further including non-nucleic acid conjugates.

The present invention provides compounds having reactive phosphorus groups useful for forming internucleoside linkages including for example phosphodiester and phosphorothioate internucleoside linkages. Methods of preparation and/or purification of precursors or antisense compounds of the instant invention are not a limitation of the compositions or methods of the invention. Methods for synthesis and purification of DNA, RNA, and the antisense compounds of the instant invention are well known to those skilled in the art.

As used herein the term "chimeric antisense compound" refers to an antisense compound, having at least one sugar, nucleobase and/or internucleoside linkage that is differentially modified as compared to the other sugars, nucleobases and internucleoside linkages within the same oligomeric compound. The remainder of the sugars, nucleobases and internucleoside linkages can be independently modified or unmodified. In general a chimeric oligomeric compound will have modified nucleosides that can be in isolated positions or grouped together in regions that will define a particular motif. Any combination of modifications and or mimetic groups can comprise a chimeric oligomeric compound of the present invention.

Chimeric oligomeric compounds typically contain at least one region modified so as to confer increased resistance to nuclease degradation, increased cellular uptake, and/or increased binding affinity for the target nucleic acid. An additional region of the oligomeric compound may serve as a substrate for enzymes capable of cleaving RNA:DNA or RNA:RNA hybrids. By way of example, RNase H is a cellular endonuclease that cleaves the RNA strand of an RNA:DNA duplex. Activation of RNase H, therefore, results in cleavage of the RNA target, thereby greatly enhancing the efficiency of inhibition of gene expression. Consequently, comparable results can often be obtained with shorter oligomeric compounds when chimeras are used, compared to for example phosphorothioate deoxyoligonucleotides hybridizing to the same target region. Cleavage of the RNA target can be routinely detected by gel electrophoresis and, if necessary, associated nucleic acid hybridization techniques known in the art.

As used in the present invention the term "fully modified motif" refers to an antisense compound comprising a contiguous sequence of nucleosides wherein essentially each nucleoside is a sugar modified nucleoside having uniform modification.

The compounds described herein contain one or more asymmetric centers and thus give rise to enantiomers, diastereomers, and other stereoisomeric configurations that may be defined, in terms of absolute stereochemistry, as (R) or (S), α or β, or as (D) or (L) such as for amino acids et al. The present invention is meant to include all such possible isomers, as well as their racemic and optically pure forms.

In one aspect of the present invention antisense compounds are modified by covalent attachment of one or more conjugate groups. Conjugate groups may be attached by reversible or irreversible attachments. Conjugate groups may be attached directly to antisense compounds or by use of a linker. Linkers may be mono- or bifunctional linkers. Such attachment methods and linkers are well known to those skilled in the art. In general, conjugate groups are attached to antisense compounds to modify one or more properties. Such considerations are well known to those skilled in the art.

Oligomer Synthesis

Oligomerization of modified and unmodified nucleosides can be routinely performed according to literature procedures for DNA (Protocols for Oligonucleotides and Analogs, Ed. Agrawal (1993), Humana Press) and/or RNA (Scaringe, Methods (2001), 23, 206-217. Gait et al., Applications of Chemically synthesized RNA in RNA: Protein Interactions, Ed. Smith (1998), 1-36. Gallo et al., Tetrahedron (2001), 57, 5707-5713).

Antisense compounds of the present invention can be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives. The invention is not limited by the method of antisense compound synthesis.

Oligomer Purification and Analysis methods oligonucleotide purification and analysis are known to those skilled in the art. Analysis methods include capillary electrophoresis (CE) and electrospray-mass spectroscopy. Such synthesis and analysis methods can be performed in multi-well plates. The method of the invention is not limited by the method of oligomer purification.

Salts, Prodrugs and Bioequivalents

The antisense compounds of the present invention comprise any pharmaceutically acceptable salts, esters, or salts of such esters, or any other functional chemical equivalent which, upon administration to an animal including a human, is capable of providing (directly or indirectly) the biologically active metabolite or residue thereof. Accordingly, for example, the disclosure is also drawn to prodrugs and pharmaceutically acceptable salts of the antisense compounds of the present invention, pharmaceutically acceptable salts of such prodrugs, and other bio equivalents.

The term "prodrug" indicates a therapeutic agent that is prepared in an inactive or less active form that is converted to an active form (i.e., drug) within the body or cells thereof by the action of endogenous enzymes, chemicals, and/or conditions. In particular, prodrug versions of the oligonucleotides of the invention are prepared as SATE ((S-acetyl-2-thioethyl) phosphate) derivatives according to the methods disclosed in WO 93/24510 or WO 94/26764. Prodrugs can also include antisense compounds wherein one or both ends comprise nucleobases that are cleaved (e.g., by incorporating phosphodiester backbone linkages at the ends) to produce the active compound.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. Sodium salts of antisense oligonucleotides are useful and are well accepted for therapeutic administration to humans. In another embodiment, sodium salts of dsRNA compounds are also provided.

Formulations

The antisense compounds of the invention may also be admixed, encapsulated, conjugated or otherwise associated with other molecules, molecule structures or mixtures of compounds.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. In a preferred embodiment, administration is topical to the surface of the respiratory tract, particularly pulmonary, e.g., by nebulization, inhalation, or insufflation of powders or aerosols, by mouth and/or nose.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers, finely divided solid carriers, or both, and then, if necessary, shaping the product (e.g., into a specific particle size for delivery). In a preferred embodiment, the pharmaceutical formulations of the instant invention are prepared for pulmonary administration in an appropriate solvent, e.g., water or normal saline, possibly in a sterile formulation, with carriers or other agents to allow for the formation of droplets of the desired diameter for delivery using inhalers, nasal delivery devices, nebulizers, and other devices for pulmonary delivery. Alternatively, the pharmaceutical formulations of the instant invention may be formulated as dry powders for use in dry powder inhalers.

A "pharmaceutical carrier" or "excipient" can be a pharmaceutically acceptable solvent, suspending agent or any other pharmacologically inert vehicle for delivering one or more nucleic acids to an animal and are known in the art. The excipient may be liquid or solid and is selected, with the planned manner of administration in mind, so as to provide for the desired bulk, consistency, etc., when combined with a nucleic acid and the other components of a given pharmaceutical composition.

Combinations

Compositions of the invention can contain two or more antisense compounds. In another related embodiment, compositions of the present invention can contain one or more antisense compounds, particularly oligonucleotides, targeted to a first nucleic acid and one or more additional antisense compounds targeted to a second nucleic acid target. Alternatively, compositions of the present invention can contain two or more antisense compounds targeted to different regions of the same nucleic acid target. Two or more combined compounds may be used together or sequentially. Compositions of the instant invention can also be combined with other non-antisense compound therapeutic agents.

Nonlimiting Disclosure and Incorporation by Reference

While certain compounds, compositions and methods of the present invention have been described with specificity in accordance with certain embodiments, the following examples serve only to illustrate the compounds of the invention and are not intended to limit the same. Each of the references, GenBank accession numbers, and the like recited in the present application is Incorporate herein by reference n its entirety.

EXAMPLE 1

Design of Modified Antisense Compounds Targeting SMN2

In accordance with the present invention, antisense compounds were designed to target intron 6, exon 7 or intron 7 of SMN2 (SEQ ID NO: 1). In reference to SEQ ID NO:1, nucleotides 61-114 represent exon 7, while nucleotides 1-60 and 115-174 represent portions of intron 6 and intron 7, respectively. The compounds, listed in Table 1, are either 12, 15, 16 or 18 nucleotides in length and are composed of 2'-O-methoxyethyl nucleotides, also known as 2'-MOE nucleotides. The internucleoside (backbone) linkages are phosphodiester throughout the oligonucleotide. All cytidine residues are 5-methylcytidines. Target site indicates the first (5'-most) nucleotide number of the target sequence (SEQ ID NO: 1) to which the oligonucleotide binds.

TABLE 1

2'-MOE Compounds Targeting SMN2

| ISIS # | Target Site | Target Region | Length | Sequence (5' to 3') | SEQ ID NO |
|---|---|---|---|---|---|
| 390645 | 1 | Intron 6 | 15 | TAGATAGCTATATAT | 2 |
| 393593 | 2 | Intron 6 | 15 | ATAGATAGCTATATA | 3 |
| 393592 | 3 | Intron 6 | 15 | TATAGATAGCTATAT | 4 |
| 393591 | 4 | Intron 6 | 15 | ATATAGATAGCTATA | 5 |
| 393590 | 5 | Intron 6 | 15 | GATATAGATAGCTAT | 6 |
| 393602 | 5 | Intron 6 | 12 | ATAGATAGCTAT | 7 |
| 390644 | 6 | Intron 6 | 15 | AGATATAGATAGCTA | 8 |
| 393601 | 6 | Intron 6 | 12 | TATAGATAGCTA | 9 |
| 393589 | 7 | Intron 6 | 15 | TAGATATAGATAGCT | 10 |
| 393600 | 7 | Intron 6 | 12 | ATATAGATAGCT | 11 |
| 393588 | 8 | Intron 6 | 15 | ATAGATATAGATAGC | 12 |
| 393599 | 8 | Intron 6 | 12 | GATATAGATAGC | 13 |
| 393587 | 9 | Intron 6 | 15 | TATAGATATAGATAG | 14 |
| 393598 | 9 | Intron 6 | 12 | AGATATAGATAG | 15 |
| 393586 | 10 | Intron 6 | 15 | ATATAGATATAGATA | 16 |
| 393597 | 10 | Intron 6 | 12 | TAGATATAGATA | 17 |
| 390643 | 11 | Intron 6 | 15 | TATATAGATATAGAT | 18 |
| 393596 | 11 | Intron 6 | 12 | ATAGATATAGAT | 19 |

TABLE 1-continued

2'-MOE Compounds Targeting SMN2

| ISIS # | Target Site | Target Region | Length | Sequence (5' to 3') | SEQ ID NO |
|---|---|---|---|---|---|
| 393595 | 12 | Intron 6 | 12 | TATAGATATAGA | 20 |
| 393594 | 13 | Intron 6 | 12 | ATATAGATATAG | 21 |
| 390642 | 16 | Intron 6 | 15 | ATAGCTATATAGATA | 22 |
| 390641 | 21 | Intron 6 | 15 | AAAAAATAGCTATAT | 23 |
| 390640 | 26 | Intron 6 | 15 | GTTAAAAAAAATAGC | 24 |
| 390639 | 31 | Intron 6 | 15 | AGGAAGTTAAAAAAA | 25 |
| 390638 | 36 | Intron 6 | 15 | AATAAAGGAAGTTAA | 26 |
| 390637 | 41 | Intron 6 | 15 | AGGAAATAAAGGAA | 27 |
| 390636 | 46 | Intron 6 | 15 | GTGTAAGGAAAATAA | 28 |
| 372641 | 61 | Exon 7 | 15 | ATTTTGTCTAAAACC | 29 |
| 385909 | 62 | Exon 7 | 15 | GATTTTGTCTAAAAC | 30 |
| 383497 | 63 | Exon 7 | 12 | TTTTGTCTAAAA | 31 |
| 385908 | 63 | Exon 7 | 15 | TGATTTTGTCTAAAA | 32 |
| 383496 | 64 | Exon 7 | 12 | ATTTTGTCTAAA | 33 |
| 385907 | 64 | Exon 7 | 15 | TTGATTTTGTCTAAA | 34 |
| 383495 | 65 | Exon 7 | 12 | GATTTTGTCTAA | 35 |
| 385906 | 65 | Exon 7 | 15 | TTTGATTTTGTCTAA | 36 |
| 385910 | 65 | Exon 7 | 16 | TTTTGATTTTGTCTAA | 37 |
| 372642 | 66 | Exon 7 | 15 | TTTTGATTTTGTCTA | 38 |
| 383494 | 66 | Exon 7 | 12 | TGATTTTGTCTA | 39 |
| 383493 | 67 | Exon 7 | 12 | TTGATTTTGTCT | 40 |
| 385905 | 67 | Exon 7 | 15 | TTTTTGATTTTGTCT | 41 |
| 383492 | 68 | Exon 7 | 12 | TTTGATTTTGTC | 42 |
| 385904 | 68 | Exon 7 | 15 | CTTTTTGATTTTGTC | 43 |
| 383491 | 69 | Exon 7 | 12 | TTTTGATTTTGT | 44 |
| 383490 | 70 | Exon 7 | 12 | TTTTTGATTTTG | 45 |
| 372643 | 71 | Exon 7 | 15 | CTTCTTTTTGATTTT | 46 |
| 383489 | 71 | Exon 7 | 12 | CTTTTTGATTTT | 47 |
| 383488 | 72 | Exon 7 | 12 | TCTTTTTGATTT | 48 |
| 372644 | 76 | Exon 7 | 15 | CCTTCCTTCTTTTTG | 49 |
| 372645 | 81 | Exon 7 | 15 | GAGCACCTTCCTTCT | 50 |
| 372646 | 86 | Exon 7 | 15 | AATGTGAGCACCTTC | 51 |
| 372647 | 91 | Exon 7 | 15 | TAAGGAATGTGAGCA | 52 |
| 383470 | 92 | Exon 7 | 18 | AATTTAAGGAATGTGAGC | 53 |
| 383477 | 92 | Exon 7 | 15 | TTAAGGAATGTGAGC | 54 |
| 383469 | 93 | Exon 7 | 18 | TAATTTAAGGAATGTGAG | 55 |
| 383476 | 93 | Exon 7 | 15 | TTTAAGGAATGTGAG | 56 |

TABLE 1-continued

2'-MOE Compounds Targeting SMN2

| ISIS # | Target Site | Target Region | Length | Sequence (5' to 3') | SEQ ID NO |
|---|---|---|---|---|---|
| 383487 | 93 | Exon 7 | 12 | AAGGAATGTGAG | 57 |
| 383468 | 94 | Exon 7 | 18 | TTAATTTAAGGAATGTGA | 58 |
| 383475 | 94 | Exon 7 | 15 | ATTTAAGGAATGTGA | 59 |
| 383486 | 94 | Exon 7 | 12 | TAAGGAATGTGA | 60 |
| 383467 | 95 | Exon7 | 18 | CTTAATTTAAGGAATGTG | 61 |
| 383474 | 95 | Exon 7 | 15 | AATTTAAGGAATGTG | 62 |
| 383485 | 95 | Exon 7 | 12 | TTAAGGAATGTG | 63 |
| 372648 | 96 | Exon 7 | 15 | TAATTTAAGGAATGT | 64 |
| 383466 | 96 | Exon 7 | 18 | CCTTAATTTAAGGAATGT | 65 |
| 383484 | 96 | Exon 7 | 12 | TTTAAGGAATGT | 66 |
| 383473 | 97 | Exon 7 | 15 | TTAATTTAAGGAATG | 67 |
| 383483 | 97 | Exon 7 | 12 | ATTTAAGGAATG | 68 |
| 383472 | 98 | Exon 7 | 15 | CTTAATTTAAGGAAT | 69 |
| 383482 | 98 | Exon 7 | 12 | AATTTAAGGAAT | 70 |
| 383471 | 99 | Exon 7 | 15 | CCTTAATTTAAGGAA | 71 |
| 383481 | 99 | Exon 7 | 12 | TAATTTAAGGAA | 72 |
| 372649 | 100 | Exon 7 | 15 | TCCTTAATTTAAGGA | 73 |
| 383480 | 100 | Exon 7 | 12 | TTAATTTAAGGA | 74 |
| 383479 | 101 | Exon 7 | 12 | CTTAATTTAAGG | 75 |
| 383478 | 102 | Exon 7 | 12 | CCTTAATTTAAG | 76 |
| 390646 | 115 | Intron 7 | 15 | TGCTGGCAGACTTAC | 77 |
| 390647 | 120 | Intron 7 | 15 | CATAATGCTGGCAGA | 78 |
| 393610 | 121 | Intron 7 | 15 | TCATAATGCTGGCAG | 79 |
| 393609 | 122 | Intron 7 | 15 | TTCATAATGCTGGCA | 80 |
| 393608 | 123 | Intron 7 | 15 | TTTCATAATGCTGGC | 81 |
| 387949 | 124 | Intron 7 | 20 | ATTCACTTTCATAATGCTGG | 82 |
| 393607 | 124 | Intron 7 | 15 | CTTTCATAATGCTGG | 83 |
| 393619 | 124 | Intron 7 | 12 | TCATAATGCTGG | 84 |
| 390648 | 125 | Intron 7 | 15 | ACTTTCATAATGCTG | 85 |
| 393618 | 125 | Intron 7 | 12 | TTCATAATGCTG | 86 |
| 393606 | 126 | Intron 7 | 15 | CACTTTCATAATGCT | 87 |
| 393617 | 126 | Intron 7 | 12 | TTTCATAATGCT | 88 |
| 393605 | 127 | Intron 7 | 15 | TCACTTTCATAATGC | 89 |
| 393616 | 127 | Intron 7 | 12 | GTTTCATAATGC | 90 |
| 393604 | 128 | Intron 7 | 15 | TTCACTTTCATAATG | 91 |
| 393615 | 128 | Intron 7 | 12 | ACTTTCATAATG | 92 |
| 393603 | 129 | Intron 7 | 15 | ATTCACTTTCATAAT | 93 |
| 393614 | 129 | Intron 7 | 12 | CACTTTCATAAT | 94 |
| 390649 | 130 | Intron 7 | 15 | GATTCACTTTCATAA | 95 |
| 393613 | 130 | Intron 7 | 12 | TCACTTTCATAA | 96 |
| 393612 | 131 | Intron 7 | 12 | TTCACTTTCATA | 97 |
| 393611 | 132 | Intron 7 | 12 | ATTCACTTTCAT | 98 |
| 390650 | 135 | Intron 7 | 15 | AGTAAGATTCACTTT | 99 |
| 390651 | 140 | Intron 7 | 15 | ACAAAAGTAAGATTC | 100 |
| 390652 | 145 | Intron 7 | 15 | GTTTTACAAAAGTAA | 101 |
| 390653 | 150 | Intron 7 | 15 | ATAAAGTTTTACAAA | 102 |
| 390654 | 155 | Intron 7 | 15 | AAACCATAAAGTTTT | 103 |
| 390655 | 160 | Intron 7 | 15 | TCCACAAACCATAAA | 104 |

Other nucleic acid sequences for SMN genes are publicly available and well known in the art. For example, Genbank Accession Nos. NM_000344, NM_022874, NM_022875, U43883, AC140134, AC139778, AC010237, AC022119 and AC004999 provide nucleotide sequences of SMN1 or SMN2.

EXAMPLE 2

Treatment with Oligomeric Compounds

When cells reach appropriate confluency, they are treated with oligonucleotide using a transfection method as described.

LIPOFECTIN™

When cells reach 65-75% confluency, they are treated with oligonucleotide. Oligonucleotide is mixed with LIPOFECTIN™ Invitrogen Life Technologies, Carlsbad, Calif.) in Opti-MEM™-1 reduced serum medium (Invitrogen Life Technologies, Carlsbad, Calif.) to achieve the desired concentration of oligonucleotide and a LIPOFECTIN™ concentration of 2.5 or 3 μg/mL per 100 nM oligonucleotide. This transfection mixture is incubated at room temperature for approximately 0.5 hours. For cells grown in 96-well plates, wells are washed once with 100 μL OPTI-MEM™-1 and then treated with 130 μL of the transfection mixture. Cells grown in 24-well plates or other standard tissue culture plates are treated similarly, using appropriate volumes of medium and oligonucleotide. Cells are treated and data are obtained in duplicate or triplicate. After approximately 4-7 hours of treatment at 37° C., the medium containing the transfection mixture is replaced with fresh culture medium.

Electroporation

When cells reach approximately 80% confluency, oligonucleotide is introduced via electroporation. Oligonucleotide concentrations used in electroporation experiments range from 0.1 to 40 μM. Cells are harvested by routine trypsinization to produce a single cell suspension. Following cell counting using a hemocytometer and pelleting by centrifugation, cells are resuspended in OPTI-MEM™-1 reduced serum medium (Invitrogen Life Technologies, Carlsbad, Calif.) to achieve a density of 1×10$^7$ cells/mL. Cells are mixed with the desired concentration of oligonucleotide and transferred to a 0.1 cm electroporation cuvette (BTX Molecular Delivery Systems, Hollister, Mass.). Cells are subjected to a single pulse using an electroporation apparatus (for example, the BTX Electro Square Porator T820 or the BTX HT300, BTX Molecular Delivery Systems, Hollister, Mass.), diluted into culture medium and plated into 24-well plates. Cells are treated and data were obtained in duplicate or triplicate.

EXAMPLE 3

Minigenes for SMN2 Splicing Studies

All SMN constructs are derivatives of pCITel (Lorson and Androphy, Hum. Mol. Genet., 2000, 9, 259-265). The primers used to generate each SMN2 construct are shown in Table 2. Using a Quickchange kit (Stratagene, La Jolla, Calif.), an XbaI site was inserted by site-directed mutagenesis at nucleotide 7170 (in intron 7) to generate pCI-SMNx-wt. For in vitro transcription studies, intron 6 was shortened by overlap-extension PCR to generate pCISMNxΔ6-wt, deleting 5,570 nt from position 1235 to the BclI site at nt 6805. Two sets of PCR were performed with Pfu polymerase and pCISMNx-wt as template. The first PCR was carried out with primers CIF1 and Δ6-bc1R, the second with primers smnΔ6-vrlp and CIR. The PCR products were purified, combined and reamplified with the outer primers (CIF1 and CIR). The final product was digested with XhoI and NotI and subcloned it into pCISMNx-wt digested with the same enzymes. All the constructs were verified by direct sequencing. Templates were generated for in vitro transcription by PCR amplification of pCISMNxΔ6-wt using primers CIF2 and smn8-75+5R. The final products contained a T7 promoter, exon 6 (124 nt), a shortened intron 6 (200 nt), exon 7 (54 nt), intron 7 (444 nt), and 75 nt of exon 8 followed by a consensus 5' splice site (GTAAGTACTT; SEQ ID NO: 22) (Cartegni and Krainer, Nature Genet., 2002, 30, 377-384; WO 02/38738).

electrophoresis. Labeled in vitro transcripts were spliced in HeLa cell nuclear or S100 extracts (Mayeda and Krainer, Methods Mol. Biol., 1999, 118, 315-321; Mayeda and Krainer, Methods Mol. Biol., 1999, 118, 309-314) by incubating 10 fmol of transcript in 12.5 μl standard splicing reactions containing 3 μl of nuclear extract or 2 μl of S100 extract. Extracts either contained no antisense oligonucleotide or were complemented with 1, 5, 10, 25, 50, 100, 200 or 400 nM of ISIS 372641, ISIS 372642, ISIS 372643, ISIS 372644, ISIS 372645, ISIS 372646, ISIS 372647, ISIS 372648 or ISIS 372649. Control oligonucleotide ISIS 372693 was also used in this study (TTGTATTCTATGTTT; SEQ ID NO: 114). The MgCl$_2$ concentration of the splicing mixture was 1.6 mM. After incubation at 30° C. for 4 h, RNA was extracted and analyzed on 8% denaturing polyacrylamide gels, followed by autoradiography and phosphorimager analysis. Exon inclusion was calculated as a percentage of the total amount of spliced mRNA (included MRNA×100/(included mRNA+ skipped mRNA).

The results showed that several of the SMN2 antisense oligonucleotides altered splicing of SMN2 exon 7, while control oligonucleotide ISIS 372693 had no effect. ISIS 372641 promoted skipping of SMN2 exon 7 in a dose-dependent manner. Exon 7 was included in only 2% of SMN2 spliced transcripts incubated with 400 nM of ISIS 372641, compared with 26% of transcripts incubated with no oligonucleotide. Similarly, ISIS 372646 inhibited inclusion of exon 7 in a dose-dependent manner with 16% of SMN2 spliced transcripts containing exon 7, compared with 32% of transcripts incubated without oligonucleotide. In contrast, ISIS 372642 inhibited skipping of exon 7 in a dose-dependent

TABLE 2

Primers used to generate SMN2 minigenes and templates

| Construct | Primer Name | Primer Sequence | SEQ ID NO |
|---|---|---|---|
| pCI-SMNx-wt | smnI7xbaF | AGATAAAAGGTTAATCTAGATCCCTACTAGAATTCTC | 106 |
| pCI-SMNx-wt | snmI7xbaR | GAGAATTCTAGTAGGGATCTAGATTAACCTTTTATCT | 107 |
| pCISMNxΔ6-wt | CIF1 | AATTGCTAACGCAGTCAGTGCTTC | 108 |
| pCISMNxΔ6-wt | Δ6-bc1R | AATATGATCAGCAAAACAAAGTCACATAACTAC | 109 |
| pCISMNxΔ6-wt | smnΔ6-vrlp | GTGACTTTGTTTTGCTGATCATATTTTGTTGAATAAAATAAG | 110 |
| pCISMNxΔ6-wt | CIR | AATGTATCTTATCATGTCTGCTCG | 111 |
| In vitro templates | CIF2 | AATGTATCTTATCATGTCTGCTCG | 112 |
| In vitro templates | Smn8-75 + 5'R | AAGTACTTACCTGTAACGCTTCACATTCCAGATCTGTC | 113 |

EXAMPLE 4

Effect of Antisense Compounds on SMN2 Splicing in Cell-free Extracts

2'-MOE antisense compounds designed to target exon 7 of SMN2 were evaluated for their effect on splicing of SMN2. Templates for in vitro SMN2 splicing studies were generated as described in Example 3. 5'-capped T7 runoff transcripts from purified PCR products were uniformly labeled with [α-$^{32}$P]-UTP and purified by denaturing polyacrylamide gel manner. The percentage of SMN2 spliced transcripts containing exon 7 increased from 28% when incubated without oligonucleotide to 40% when incubated with 400 nM of ISIS 372642. ISIS 372648 also increased inclusion of exon 7 with 69% of SMN2 transcripts containing exon 7 when incubated with the highest concentration of oligonucleotide, compared with 42% of transcripts when incubated without oligonucleotide. Extracts containing ISIS 372643 also showed a slight increase in exon 7 inclusion at the higher oligonucleotide concentrations. Taken together, these results illustrate that antisense oligonucleotides targeting exon 7 of SMN2 are capable of altering splicing of transcripts to either promote or inhibit inclusion of exon 7.

EXAMPLE 5

Effect of Antisense Compounds on SMN2 Splicing in HEk293 Cells

Antisense compounds targeting SMN2 exon 7 were evaluated for their effects on SMN2 splicing in cultured cells. HEK293 cells were electroporated with 10 µg SMN2 minigene and 10 µM of either SMN2 antisense oligonucleotide ISIS 372641, ISIS 372642, ISIS 372643, ISIS 372644, ISIS 372645, ISIS 372646, ISIS 372647, ISIS 372648 or ISIS 372649, or control oligonucleotide ISIS 372693. Sixty hours after transfection, total RNA was isolated using Trizol Reagent (Invitrogen, Carlsbad, Calif.) following the manufacturer's directions. One µg of DNAse-treated total RNA was used to generate first-strand cDNA sequences with oligo (dT) and Superscript II reverse transcriptase (Invitrogen), and the cDNA was amplified semi-quantitatively by 16 PCR cycles (94° C. for 30 s, 57.5° C. for 30 s, 72° C. for 90 s) in the presence of [α-$^{32}$P]dCTP (Lorson and Androphy, Hum. Mol. Genet., 2000, 9, 259-265). PCR products were analyzed by electrophoresis on 6% denaturing polyacrylamide gels, followed by autoradiography and phosphorimager analysis. Exon inclusion was calculated as a percentage of the total amount of spliced mRNA (included mRNA×100/(included mRNA+skipped mRNA). The percentage of SMN2 spliced transcripts containing exon 7 (% inclusion) is shown in Table 3. The target site of each oligonucleotide relative to SEQ ID NO: 1 is also indicated.

TABLE 3

Effect of SMN2 antisense compounds on exon 7 inclusion

| ISIS # | Target Site | % Inclusion |
|---|---|---|
| 372641 | 61 | 6.4 |
| 372642 | 66 | 67.4 |
| 372643 | 71 | 34.9 |
| 372644 | 76 | 12.9 |
| 372645 | 81 | 7.8 |
| 372646 | 86 | 11.8 |
| 372647 | 91 | 9.5 |
| 372648 | 96 | 75.2 |
| 372649 | 100 | 55.1 |
| 372693 | Control | 57.7 |

Compared to control oligonucleotide, transfection with either ISIS 372642 or 372648 resulted in a greater percentage of SMN2 transcripts with exon 7 included, which is consistent with results obtained from in vitro assays. Treatment with ISIS 372641, ISIS 372644, ISIS 372645, ISIS 372646 and ISIS 372647 resulted in the most significant increase in exon 7 skipping.

SMN2 antisense oligonucleotides were further evaluated for their effects on endogenous SMN1 and SMN2 pre-mRNA splicing in cultured cells. HEK293 cells were electroporated with 10 µM of either SMN2 antisense oligonucleotide ISIS 372641, ISIS 372642, ISIS 372643, ISIS 372644, ISIS 372645, ISIS 372646, ISIS 372647, ISIS 372648 or ISIS 372649, or control oligonucleotide ISIS 372693. Sixty hours after transfection, RNA was isolated and RT-PCR was performed as described above to examine splicing changes of both SMN1 and SMN2 pre-mRNAs. PCR products were digested with DdeI to distinguish between SMN1 and SMN2, separated by electrophoresis on 6% denaturing polyacrylamide gels and analyzed by autoradiography. The percentage of SMN1 and SMN2 spliced transcripts containing exon 7 (% inclusion) is shown in Table 4.

TABLE 4

Effect of SMN2 antisense oligonucleotides on SMN1 and SMN2 pre-mRNA splicing

| ISIS # | % Inclusion SMN1 | % Inclusion SMN2 |
|---|---|---|
| 372641 | 82.5 | 11.1 |
| 372642 | 96.2 | 69.5 |
| 372643 | 94.1 | 28.8 |
| 372644 | 68.5 | 23.8 |
| 372645 | 47.3 | 15.2 |
| 372646 | 57.7 | 20.2 |
| 372647 | 58.8 | 12.8 |
| 372648 | 93.1 | 52.2 |
| 372649 | 94.8 | 49.3 |
| 372693 | 95.1 | 50.1 |

In accordance with previous results, transfection with ISIS 372642 and ISIS 372648 led to the greatest level of exon 7 inclusion in SMN2 pre-mRNA transcripts. ISIS 372641, ISIS 372644, ISIS 372645, ISIS 372646 and ISIS 372647 significantly reduced the percentage of SMN1 transcripts containing exon 7. These oligonucleotides, along with ISIS 372643, also reduced exon 7 inclusion in SMN2 mRNAs.

Additional antisense oligonucleotides targeting the 3' end of SMN2 exon 7 (see Table 1) were evaluated for their effects on SMN2 pre-mRNA splicing. HEK293 cells were electroporated with 10 µM of either SMN2 antisense oligonucleotide ISIS 383466, ISIS 383467, ISIS 383468, ISIS 383469, ISIS 383470, ISIS 383471, ISIS 383472, ISIS 383473, ISIS 383474, ISIS 383475, ISIS 383476, ISIS 383477 or ISIS 372648, or a control oligonucleotide. Fifty hours after transfection, RNA was isolated and RT-PCR was performed as described above to examine splicing changes of SMN2 pre-mRNA. PCR products were digested with DdeI to distinguish between SMN1 and SMN2, separated by electrophoresis on 6% denaturing polyacrylamide gels and analyzed by autoradiography. The percentage of SMN2 spliced transcripts containing exon 7 (% inclusion) is shown in Table 5. The length and target site of each oligonucleotide relative to SEQ ID NO: 1 are also indicated.

TABLE 5

Effect of SMN2 antisense oligonucleotides on SMN2 pre-mRNA splicing

| ISIS # | Target Site | Length | % Inclusion |
|---|---|---|---|
| 383470 | 92 | 18 | 4.9 |
| 383477 | 92 | 15 | 5.3 |
| 383469 | 93 | 18 | 18.9 |
| 383476 | 93 | 15 | 32.8 |
| 383468 | 94 | 18 | 18.7 |
| 383475 | 94 | 15 | 84.8 |
| 383467 | 95 | 18 | 8.1 |
| 383474 | 95 | 15 | 77.0 |
| 372648 | 96 | 15 | 59.6 |
| 383466 | 96 | 18 | 37.5 |
| 383473 | 97 | 15 | 42.2 |
| 383472 | 98 | 15 | 45.0 |
| 383471 | 99 | 15 | 37.1 |
| Control | N/A | N/A | 41.3 |
| Vehicle | N/A | N/A | 41.4 |

The results demonstrate that a number of SMN2 antisense oligonucleotides can alter splicing of SMN2 pre-mRNAs. ISIS 383467, ISIS 383468, ISIS 383469, ISIS 383470, ISIS 383476 and ISIS 383477 inhibited inclusion of exon 7; ISIS 383474, ISIS 383475 and ISIS 372648 significantly increased inclusion of exon 7; and ISIS 383466, ISIS 383471, ISIS 383472 and ISIS 383473 appeared to have little effect on SMN2 splicing, relative to oligonucleotide and vehicle controls. These results suggest that SMN2 oligonucleotides with a target site between nucleotides 94-96 are particularly effective at achieving inclusion of exon 7 during SMN2 pre-mRNA splicing, and further suggests oligonucleotides 15 nucleotides in length are more effective an those 11 nucleotides in length.

EXAMPLE 6

Effect of Antisense Compounds on SMN2 Splicing in SMA Fibroblast Cells

In accordance with the present invention, SMN2 antisense oligonucleotides were tested in fibroblast cells derived from a patient with type I SMA (3813 cell line; Coovert et al., Human Mol. Genet., 1997, 6, 1205-1214). SMA fibroblasts contain SMN2, but do not express SMN1. SMA fibroblasts were lipofected with 200 nM of either SMN2 antisense oligonucleotide ISIS 372641, ISIS 372642, ISIS 372643, ISIS 372644, ISIS 372645, ISIS 372646, ISIS 372647, ISIS 372648 or ISIS 372649, or control oligonucleotide ISIS 372693. Seventy hours after transfection, RNA was isolated and RT-PCR was performed as described above to examine splicing changes of endogenous SMN2 pre-mRNAs. PCR products were separated by electrophoresis and analyzed by autoradiography. The percentage of SMN2 spliced transcripts containing exon 7 (% inclusion) is shown in Table 6. The target site of each oligonucleotide relative to SEQ ID NO: 1 is also indicated.

TABLE 6

Effect of SMN2 antisense oligonucleotides on exon 7 inclusion in SMA fibroblasts

| ISIS # | Target Site | % Inclusion |
|---|---|---|
| 372641 | 61 | 41.8 |
| 372642 | 66 | 55.2 |
| 372643 | 71 | 40.9 |
| 372644 | 76 | 43.4 |
| 372645 | 81 | 43.7 |
| 372646 | 86 | 38.8 |
| 372647 | 91 | 43.6 |
| 372648 | 96 | 49.8 |
| 372649 | 100 | 48.8 |
| 372693 | Control | 48.7 |
| PBS | N/A | 48.8 |

In accordance with previous findings, treatment with ISIS 372642 and ISIS 372648 generated a greater percentage of SMN2 splicing products containing exon 7.

A second experiment to further evaluate ISIS 372642 and ISIS 383475 in SMA fibroblasts was performed. SMA fibroblasts were lipofected with either 200 nM ISIS 372642, 200 nM ISIS 383475, or 100 nM ISIS 372642 in combination with 100 nM ISIS 383475. ISIS 372693 (200 nM) and vehicle only were also used as controls. Fifty hours after transfection, RNA was isolated and RT-PCR was performed. PCR products were separated by electrophoresis and analyzed by autoradiography. The percentage of SMN2 spliced transcripts containing exon 7 (% inclusion) is shown in Table 7.

TABLE 7

Effect of ISIS 372642 and ISIS 383475 on exon 7 inclusion in SMA fibroblasts

| Treatment (ISIS #) | % Inclusion |
|---|---|
| 372642 | 47.8 |
| 383475 | 53.9 |
| 372642 & 383475 | 49.2 |
| 372693 | 36.3 |
| Vehicle | 35.0 |

The results demonstrate that treatment with ISIS 372642 or ISIS 383475, either alone or in combination, leads to greater inclusion of exon 7 in SMA transcripts.

EXAMPLE 7

Microwalk of ISIS 372642 and ISIS 372648 Target Sites

The studies shown above demonstrated that both ISIS 372642 and ISIS 372648 were effective in promoting SMN2 exon 7 inclusion. To further evaluate the target sites surrounding these compounds, additional compounds were designed as 1 nucleotide microwalks around each site (see Table 1 for sequences and target sites). Ten compounds 12 nucleotides in length were designed for each microwalk. Seven additional compounds 15 or 16 nucleotides in length were designed to target the region of ISIS 372642. The antisense compounds targeting the 3' end of exon 7 (ISIS 383466-382477), described above in Example 5, were included for comparison with the ISIS 372648 microwalk compounds. Each compound was evaluated in the SMN2 minigene splicing assay and the endogenous SMN1/SMN2 splicing assay in HEK293 cells. Both assays are described in previous examples herein. The results are in shown in Tables 8 and 9.

TABLE 8

ISIS 372642 Microwalk Compounds: Effect on Exon 7 Inclusion

| ISIS # | Target Site | Length | % Inclusion SMN2 Minigene | % Inclusion Endogenous SMN2 | % Inclusion Endogenous SMN1 |
|---|---|---|---|---|---|
| 385909 | 62 | 15 | 44 | 43 | 81 |
| 383497 | 63 | 12 | 55 | 51 | 86 |
| 385908 | 63 | 15 | 49 | 53 | 85 |
| 383496 | 64 | 12 | 32 | 36 | 81 |
| 385907 | 64 | 15 | 56 | 54 | 86 |
| 383495 | 65 | 12 | 54 | 49 | 85 |
| 385906 | 65 | 15 | 56 | 57 | 87 |
| 385910 | 65 | 16 | 60 | 66 | 89 |
| 372642 | 66 | 15 | 66 | 74 | 89 |
| 383494 | 66 | 12 | 57 | 51 | 86 |
| 383493 | 67 | 12 | 57 | 52 | 85 |
| 385905 | 67 | 15 | 74 | 85 | 89 |
| 383492 | 68 | 12 | 60 | 56 | 85 |
| 385904 | 68 | 15 | 9 | 6 | 19 |
| 383491 | 69 | 12 | 38 | 41 | 81 |
| 383490 | 70 | 12 | 51 | 49 | 84 |
| 383489 | 71 | 12 | 13 | 27 | 76 |
| 383488 | 72 | 12 | 24 | 38 | 82 |
| Control | N/A | N/A | 52 | 51 | 86 |
| Control | N/A | N/A | 53 | 50 | 86 |

TABLE 9

ISIS 372648 Microwalk Compounds: Effect on Exon 7 Inclusion

| ISIS # | Target Site | Length | % Inclusion SMN2 Minigene | % Inclusion Endogenous SMN2 | % Inclusion Endogenous SMN1 |
|---|---|---|---|---|---|
| 383470 | 92 | 18 | 8 | 12 | 63 |
| 383477 | 92 | 15 | 6 | 7 | 38 |
| 383469 | 93 | 18 | 29 | 26 | 89 |
| 383476 | 93 | 15 | 36 | 31 | 87 |
| 383487 | 93 | 12 | 11 | 16 | 79 |
| 383468 | 94 | 18 | 31 | 26 | 88 |
| 383475 | 94 | 15 | 85 | 88 | 96 |
| 383486 | 94 | 12 | 44 | 41 | 91 |
| 383467 | 95 | 18 | 14 | 13 | 82 |
| 383474 | 95 | 15 | 79 | 71 | 94 |
| 383485 | 95 | 12 | 63 | 60 | 93 |
| 372648 | 96 | 15 | 70 | 57 | 93 |
| 383466 | 96 | 18 | 38 | 43 | 92 |
| 383484 | 96 | 12 | 65 | 56 | 92 |
| 383473 | 97 | 15 | 62 | 53 | 94 |
| 383483 | 97 | 12 | 63 | 56 | 94 |
| 383472 | 98 | 15 | 41 | 46 | 93 |
| 383482 | 98 | 12 | 59 | 45 | 94 |
| 383471 | 99 | 15 | 38 | 47 | 92 |
| 383481 | 99 | 12 | 42 | 46 | 92 |
| 383480 | 100 | 12 | 39 | 48 | 91 |
| 383479 | 101 | 12 | 44 | 44 | 92 |
| 383478 | 102 | 12 | 47 | 41 | 93 |
| Control | N/A | N/A | 41 | 44 | 93 |
| Control | N/A | N/A | 44 | 48 | 92 |

In accordance with previous results, treatment with ISIS 372642, ISIS 372648 or ISIS 383475 led to a significant increase in exon 7 inclusion. In addition, ISIS 385905 was identified as a particularly effective compound for promoting exon 7 inclusion. To further evaluate ISIS 385905 and ISIS 383475, dose-response and duration of action studies were performed. To determine the effect of oligonucleotide dose, HEK293 cells were electroporated with either ISIS 385905 or ISIS 383475 at a concentration of 0, 0.2, 0.5, 1, 2, 5, 10 or 20 M. Sixty hours after electroporation, RNA was isolated and RT-PCR was performed as described above to determine the extent exon 7 inclusion. The results, expressed as % inclusion of exon 7, are shown in Table 10.

TABLE 10

Dose-response of ISIS 385905 and ISIS 383475

| ISIS # | 0 µM | 0.2 µM | 0.5 µM | 1.0 µM | 2.0 µM | 5.0 µM | 10 µM | 20 µM |
|---|---|---|---|---|---|---|---|---|
| 385905 | 50 | 53 | 61 | 65 | 74 | 78 | 82 | 87 |
| 383475 | 51 | 57 | 65 | 72 | 77 | 83 | 87 | 89 |

The results show a dose-dependent increase in exon 7 inclusion following treatment with either compound. To assess duration of action, HEK293 cells were electroporated with 10 µM of either compound and RNA was isolated and subjected to RT-PCR at day 0, 1, 2, 3, 4 and 5. The results, expressed as % inclusion of exon 7, are shown in Table 11.

TABLE 11

Duration of Action of ISIS 385905 and ISIS 383475

| ISIS # | Day 0 | Day 1 | Day 2 | Day 3 | Day 4 | Day 5 |
|---|---|---|---|---|---|---|
| 385905 | 49 | 80 | 83 | 82 | 85 | 79 |
| 383475 | 48 | 84 | 89 | 88 | 89 | 83 |

These results demonstrate a significant increase in exon 7 inclusion following treatment of either compound, and further show the compounds are effective for at least five days.

Taken together, the results of the experiments detailed above demonstrate that antisense compounds having a target site (5'-most nucleotide to which the compound binds) of nucleotides 64-68 or 94-97 of SEQ ID NO: 1 are most effective at promoting exon 7 inclusion in SMN2 transcripts. The target sites of these compounds overlap with predicted ESS (exonic splicing silencer) elements, without having significant overlap with predicted ESE (exonic splicing enhancer) elements. Thus, the antisense compounds described herein may function by blocking binding of trans splicing factors to particular cis regulatory elements, thereby influencing splice site selection and specifically, inclusion or exclusion of exon 7 from SMN2 mRNAs.

EXAMPLE 8

Effect of Compounds Targeting Exon 7 or Intron 7 on Inclusion of Exon 7

In previous examples herein, antisense compounds ISIS 372642, ISIS 385905 and ISIS 383475, each of which target exon 7, were shown to significantly increase inclusion of SMN2 exon 7. These exon 7-targeted compounds and a compound targeting SMN2 intron 7 (ISIS 387949) were compared for their capacity to promote exon 7 inclusion. As described in previous examples herein, HEK293 cells were electroporated with 10 µM of oligonucleotide and RT-PCR was performed after two days to examine splicing changes of endogenous SMN1 and SMN2. In comparison to control oligonucleotide, the compounds targeted to exon 7 exhibited a significant increase in exon 7 inclusion, as expected. In addition, the intron 7 targeted compound led to incorporation of exon 7 in nearly all SMN1 and SMN2 mRNAs. These results suggest antisense compounds targeted to intronic sequences also contribute to incorporation of SMN2 exon 7. Intronic sequences also are known to contain splicing regulatory elements (i.e. intronic splicing enhancers and intronic splicing silencers), providing a possible mechanism of action for ISIS 387949.

EXAMPLE 9

Systematic Mapping of Intronic Splicing Silencers (ISSs)

To further investigate whether antisense compounds targeting the introns flanking exon 7 of SMN2 could alter inclusion of exon 7, such as by interfering with intronic splicing silencers, compounds were designed to target the 60 nucleotides of intron 6 (nucleotides 1-60 of SEQ ID NO: 1) or the 60 nucleotides of intron 7 (nucleotides 115-174 of SEQ ID NO: 1) immediately adjacent to exon 7. Antisense compounds targeting intron 6 (ISIS 390636, ISIS 390637, ISIS 390638, ISIS 390639, ISIS 390640, ISIS 390641, ISIS 390642, ISIS 390643, ISIS 390644 and ISIS 390645) or intron 7 (ISIS 390646, ISIS 390647, ISIS 390648, ISIS 390649, ISIS 390650, ISIS 390651, ISIS 390652, ISIS 390653, ISIS 390654 and ISIS 390655) are show above in Table 1. Each compound was tested in three different assays to evaluate their effect on exon 7 inclusion: SMN2 minigene splicing in cell-free extracts, SMN2 minigene splicing in transfected HEK293 cells and splicing of endogenous SMN2 in HEK293 cells. The results obtained from the three assays demonstrated that several antisense compounds were able to increase inclusion of exon 7. In particular, ISIS 390644 and ISIS 390648 were the most effect intron 6 and intron 7-targeted compounds, respectively.

To further investigate the regions targeted by ISIS 390644 and ISIS 390648, additional compounds were designed as microwalks around these target sequences (see Table 1 for sequences). For these experiments, compounds 12 and 15 nucleotides in length were designed and tested in accordance with the procedures detailed in previous examples herein. Compounds targeting the region of ISIS 390644 (intron 6) were tested in the in vitro SMN2 minigene assay and endogenous SMN1/SMN2 assay in HEK293 cells. The results are shown in Table 12.

TABLE 12

Results of Microwalk of Intron 6 Compound ISIS 390644

| ISIS # | Target Site | Length | % Inclusion SMN2 minigene | % Inclusion Endogenous SMN2 |
|---|---|---|---|---|
| 393586 | 10 | 15 | 10 | 32 |
| 393587 | 9 | 15 | 18 | 44 |
| 393588 | 8 | 15 | 32 | 60 |
| 393589 | 7 | 15 | 59 | 79 |
| 390644 | 6 | 15 | 65 | 75 |
| 393590 | 5 | 15 | 49 | 67 |
| 393591 | 4 | 15 | 20 | 46 |
| 393592 | 3 | 15 | 22 | 44 |
| 393593 | 2 | 15 | 29 | 50 |
| 393594 | 13 | 12 | 20 | 44 |
| 393595 | 12 | 12 | 13 | 39 |
| 393596 | 11 | 12 | 15 | 44 |
| 393597 | 10 | 12 | 13 | 39 |
| 393598 | 9 | 12 | 17 | 48 |
| 393599 | 8 | 12 | 30 | 64 |
| 393600 | 7 | 12 | 28 | 62 |
| 393601 | 6 | 12 | 44 | 63 |
| 393602 | 5 | 12 | 29 | 46 |
| Control | N/A | N/A | 22 | 43 |

As shown in Table 12, antisense compounds having a target site of nucleotides 5-8 (SEQ ID NO: 1) results in the greatest percentage of transcripts containing exon 7. These findings suggest this region of intron 6 contains an intronic splicing silencer, which normally functions to inhibit inclusion of exon 7. Upon blockade of this regulatory element, splice site selection is altered to promote exon 7 inclusion.

Compounds targeting the region of 390648 (intron 7) were assayed using the SMN2 minigene in vitro and in transfected HEK293 cells and tested in the endogenous SMN2 splicing assay in HEK293 cells. The results are shown in Table 13.

TABLE 13

Results of Microwalk of Intron 7 Compound ISIS 390648

| ISIS # | Target Site | Length | % Inclusion SMN2 in vitro minigene | % Inclusion SMN2 minigene | % Inclusion Endogenous SMN2 |
|---|---|---|---|---|---|
| 393603 | 129 | 15 | 43 | 51 | 76 |
| 393604 | 128 | 15 | 46 | 75 | 97 |

TABLE 13-continued

Results of Microwalk of Intron 7 Compound ISIS 390648

| ISIS # | Target Site | Length | % Inclusion SMN2 in vitro minigene | % Inclusion SMN2 minigene | % Inclusion Endogenous SMN2 |
|---|---|---|---|---|---|
| 393605 | 127 | 15 | 57 | 97 | 100 |
| 393606 | 126 | 15 | 56 | 97 | 100 |
| 390648 | 125 | 15 | 53 | 98 | 100 |
| 393607 | 124 | 15 | 67 | 100 | 100 |
| 393608 | 123 | 15 | 75 | 100 | 100 |
| 393609 | 122 | 15 | 60 | 97 | 100 |
| 393610 | 121 | 15 | 54 | 58 | 78 |
| 393611 | 132 | 12 | 41 | 17 | 40 |
| 393612 | 131 | 12 | 39 | 30 | 58 |
| 393613 | 130 | 12 | 42 | 43 | 64 |
| 393614 | 129 | 12 | 48 | 43 | 64 |
| 393615 | 128 | 12 | 38 | 36 | 44 |
| 393616 | 127 | 12 | 38 | 30 | 90 |
| 393617 | 126 | 12 | 36 | 30 | 92 |
| 393618 | 125 | 12 | 44 | 71 | 97 |
| 393619 | 124 | 12 | 69 | 92 | 97 |
| Control | N/A | N/A | 28 | 23 | 44 |

While all compounds led to an increase in exon 7 inclusion, compounds with target sites between nucleotides 121 and 129 (SEQ ID NO: 1) were most effective.

Select compounds targeting intron 7 were further evaluated for SMN2 exon 7 inclusion following transfection at a low oligonucleotide dose of 0.1 µM. As previously described herein, HEK293 cells were electroporated with ISIS 393605, ISIS 393606, ISIS 390648, ISIS 393607, ISIS 393608, ISIS 393609, ISIS 393617, ISIS 393618 or ISIS 393619 and levels of endogenous SMN2 splice products were determined. The results are shown in Table 14.

TABLE 14

Effect on SMN2 Exon 7 Incorporation Following Low-Dose Treatment

| ISIS # | Target Site | Length | % Inclusion Endogenous SMN2 |
|---|---|---|---|
| 393605 | 127 | 15 | 56 |
| 393606 | 126 | 15 | 58 |
| 390648 | 125 | 15 | 60 |
| 393607 | 124 | 15 | 60 |
| 393608 | 123 | 15 | 63 |
| 393609 | 122 | 15 | 53 |
| 393617 | 126 | 12 | 51 |
| 393618 | 125 | 12 | 51 |
| 393619 | 124 | 12 | 57 |
| Control | N/A | N/A | 49 |

As shown in Table 14, even at a very low dose, antisense compounds targeting intron 7 are effective at promoting inclusion of exon 7. Taken together, these results suggest the region near the 5' end of intron 7 (encompassing nucleotides 121-129 of SEQ ID NO: 1) contains an intronic splicing silencer.

What is claimed is:

1. An antisense oligonucleotide having a nucleotide sequence at least 90% complementary to a target region of SEQ ID NO: 1 as measured over the entirety of the antisense oligonucleotide, wherein:
the 5'-most nucleotide of the target region is nucleotide 121, 122, 123, 124, 125, 126, 127, 128 or 129 of SEQ ID NO: 1;
the antisense oligonucleotide is 12 to 20 nucleotides in length; and
each nucleoside of the antisense oligonucleotide comprises a 2'-O-methoxyethyl sugar modification.

2. The antisense oligonucleotide of claim 1 that is 12 nucleotides in length.

3. The antisense oligonucleotide of claim 1 that is 15 nucleotides in length.

4. The antisense oligonucleotide of claim 1 that is 18 nucleotides in length.

5. The antisense oligonucleotide of claim 1 that is 20 nucleotides in length.

6. The antisense oligonucleotide of claim 1 comprising at least one phosphorothioate linkage.

7. The antisense oligonucleotide of claim 1 that is 100% complementary to the target region of SEQ ID NO: 1.

8. The antisense oligonucleotide of claim 7 that is 12 nucleotides in length.

9. The antisense oligonucleotide of claim 7 that is 15 nucleotides in length.

10. The antisense oligonucleotide of claim 7 that is 18 nucleotides in length.

11. The antisense oligonucleotide of claim 7 that is 20 nucleotides in length.

12. The antisense oligonucleotide of claim 7 comprising at least one phosphorothioate linkage.

13. An antisense oligonucleotide having a nucleotide sequence 100% complementary to a target region of SEQ ID NO: 1 as measured over the entirety of the antisense oligonucleotide, wherein:
the 5'-most nucleotide of the target region is nucleotide 123 of SEQ ID NO: 1;
the antisense oligonucleotide is 12 to 20 nucleotides in length; and
each nucleoside of the antisense oligonucleotide comprises a 2'-O-methoxyethyl sugar modification.

14. The antisense oligonucleotide of claim 13 that is 12 nucleotides in length.

15. The antisense oligonucleotide of claim 13 that is 15 nucleotides in length.

16. The antisense oligonucleotide of claim 13 that is 18 nucleotides in length.

17. The antisense oligonucleotide of claim 13 that is 20 nucleotides in length.

18. The antisense oligonucleotide of claim 13 comprising at least one phosphorothioate linkage.

19. An antisense oligonucleotide having a nucleotide sequence 100% complementary to a target region of SEQ ID NO: 1 as measured over the entirety of the antisense oligonucleotide, wherein:
the 5'-most nucleotide of the target region is nucleotide 124 of SEQ ID NO: 1;
the antisense oligonucleotide is 12 to 20 nucleotides in length; and
each nucleoside of the antisense oligonucleotide comprises a 2'-O-methoxyethyl sugar modification.

20. The antisense oligonucleotide of claim 19 that is 12 nucleotides in length.

21. The antisense oligonucleotide of claim 19 that is 15 nucleotides in length.

22. The antisense oligonucleotide of claim 19 that is 18 nucleotides in length.

23. The antisense oligonucleotide of claim 19 that is 20 nucleotides in length.

24. The antisense oligonucleotide of claim 19 comprising at least one phosphorothioate linkage.

25. The antisense oligonucleotide of claim 22 comprising at least one phosphorothioate linkage.

26. The antisense oligonucleotide of claim 25 wherein each internucleoside linkage is a phosphorothioate linkage.

27. An antisense oligonucleotide having a nucleotide sequence 100% complementary to a target region of SEQ ID NO: 1 as measured over the entirety of the antisense oligonucleotide, wherein:
the 5'-most nucleotide of the target region is nucleotide 125 of SEQ ID NO: 1;
the antisense oligonucleotide is 12 to 20 nucleotides in length; and
each nucleoside of the antisense oligonucleotide comprises a 2'-O-methoxyethyl sugar modification.

28. The antisense oligonucleotide of claim 27 that is 12 nucleotides in length.

29. The antisense oligonucleotide of claim 27 that is 15 nucleotides in length.

30. The antisense oligonucleotide of claim 27 that is 18 nucleotides in length.

31. The antisense oligonucleotide of claim 27 that is 20 nucleotides in length.

32. The antisense oligonucleotide of claim 27 comprising at least one phosphorothioate linkage.

33. An antisense oligonucleotide targeted to intron 7 of a nucleic acid molecule encoding SMN2, wherein:
the antisense oligonucleotide comprises SEQ ID NO: 84 and is at least 90% complementary to the nucleic acid molecule encoding SMN2 as measured over the entirety of the antisense oligonucleotide;
the antisense oligonucleotide is 12 to 20 nucleotides in length; and
each nucleoside of the antisense oligonucleotide comprises a 2'-O-methoxyethyl sugar modification.

34. The antisense oligonucleotide of claim 33 that is 12 nucleotides in length.

35. The antisense oligonucleotide of claim 33 that is 15 nucleotides in length.

36. The antisense oligonucleotide of claim 33 that is 18 nucleotides in length.

37. The antisense oligonucleotide of claim 33 that is 20 nucleotides in length.

38. The antisense oligonucleotide of claim 33 comprising at least one phosphorothioate linkage.

39. The antisense oligonucleotide of claim 38 wherein each internucleoside linkage is a phosphorothioate linkage.

40. The antisense oligonucleotide of claim 35, wherein the antisense oligonucleotide comprises SEQ ID NO: 83.

41. A pharmaceutical composition comprising an antisense oligonucleotide of claim 1.

42. A pharmaceutical composition comprising an antisense oligonucleotide of claim 13.

43. A pharmaceutical composition comprising an antisense oligonucleotide of claim 19.

44. A pharmaceutical composition comprising an antisense oligonucleotide of claim 22.

45. A pharmaceutical composition comprising an antisense oligonucleotide of claim 25.

46. A pharmaceutical composition comprising an antisense oligonucleotide of claim 26.

47. A pharmaceutical composition comprising an antisense oligonucleotide of claim 27.

48. A pharmaceutical composition comprising an antisense oligonucleotide of claim 33.

\* \* \* \* \*

UNITED STATES PATENT AND TRADEMARK OFFICE
CERTIFICATE OF CORRECTION

PATENT NO.       : 8,361,977 B2
APPLICATION NO.  : 11/993609
DATED            : January 29, 2013
INVENTOR(S)      : Baker et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1434 days.

Signed and Sealed this

First Day of September, 2015

Michelle K. Lee
*Director of the United States Patent and Trademark Office*

SEQUENCE LISTING

<160> NUMBER OF SEQ ID NOS: 114

<210> SEQ ID NO 1
<211> LENGTH: 174
<212> TYPE: DNA
<213> ORGANISM: Homo sapiens -continued

```
<400> SEQUENCE: 1
atatatagct atctatatct atatagctat ttttttttaac ttcctttatt ttccttacag      60
ggttttagac aaaatcaaaa agaaggaagg tgctcacatt ccttaaatta aggagtaagt     120
ctgccagcat tatgaaagtg aatcttactt ttgtaaaact ttatggtttg tgga           174

<210> SEQ ID NO 2
<211> LENGTH: 15
<212> TYPE: DNA
<213> ORGANISM: Artificial Sequence
<220> FEATURE:
<223> OTHER INFORMATION: Antisense Compound

<400> SEQUENCE: 2
tagatagcta tatat                                                       15

<210> SEQ ID NO 3
<211> LENGTH: 15
<212> TYPE: DNA
<213> ORGANISM: Artificial Sequence
<220> FEATURE:
<223> OTHER INFORMATION: Antisense Compound

<400> SEQUENCE: 3
atagatagct atata                                                       15

<210> SEQ ID NO 4
<211> LENGTH: 15
<212> TYPE: DNA
<213> ORGANISM: Artificial Sequence
<220> FEATURE:
<223> OTHER INFORMATION: Antisense Compound

<400> SEQUENCE: 4
tatagatagc tatat                                                       15

<210> SEQ ID NO 5
<211> LENGTH: 15
<212> TYPE: DNA
<213> ORGANISM: Artificial Sequence
<220> FEATURE:
<223> OTHER INFORMATION: Antisense Compound

<400> SEQUENCE: 5
atatagatag ctata                                                       15

<210> SEQ ID NO 6
<211> LENGTH: 15
<212> TYPE: DNA
<213> ORGANISM: Artificial Sequence
<220> FEATURE:
<223> OTHER INFORMATION: Antisense Compound

<400> SEQUENCE: 6
gatatagata gctat                                                       15

<210> SEQ ID NO 7
<211> LENGTH: 12
<212> TYPE: DNA
<213> ORGANISM: Artificial Sequence
<220> FEATURE:
<223> OTHER INFORMATION: Antisense Compound

<400> SEQUENCE: 7
atagatagct at                                                          12
```

<210> SEQ ID NO 8
<211> LENGTH: 15
<212> TYPE: DNA
<213> ORGANISM: Artificial Sequence
<220> FEATURE:
<223> OTHER INFORMATION: Antisense Compound

<400> SEQUENCE: 8
agatatagat agcta                                                        15

<210> SEQ ID NO 9
<211> LENGTH: 12
<212> TYPE: DNA
<213> ORGANISM: Artificial Sequence
<220> FEATURE:
<223> OTHER INFORMATION: Antisense Compound

<400> SEQUENCE: 9
tatagatagc ta                                                           12

<210> SEQ ID NO 10
<211> LENGTH: 15
<212> TYPE: DNA
<213> ORGANISM: Artificial Sequence
<220> FEATURE:
<223> OTHER INFORMATION: Antisense Compound

<400> SEQUENCE: 10
tagatataga tagct                                                        15

<210> SEQ ID NO 11
<211> LENGTH: 12
<212> TYPE: DNA
<213> ORGANISM: Artificial Sequence
<220> FEATURE:
<223> OTHER INFORMATION: Antisense Compound

<400> SEQUENCE: 11
atatagatag ct                                                           12

<210> SEQ ID NO 12
<211> LENGTH: 15
<212> TYPE: DNA
<213> ORGANISM: Artificial Sequence
<220> FEATURE:
<223> OTHER INFORMATION: Antisense Compound

<400> SEQUENCE: 12
atagatatag atagc                                                        15

<210> SEQ ID NO 13
<211> LENGTH: 12
<212> TYPE: DNA
<213> ORGANISM: Artificial Sequence
<220> FEATURE:
<223> OTHER INFORMATION: Antisense Compound

<400> SEQUENCE: 13
gatatagata gc                                                           12

<210> SEQ ID NO 14
<211> LENGTH: 15
<212> TYPE: DNA
<213> ORGANISM: Artificial Sequence
<220> FEATURE:
<223> OTHER INFORMATION: Antisense Compound

```
<400> SEQUENCE: 14
tatagatata gatag                                                 15

<210> SEQ ID NO 15
<211> LENGTH: 12
<212> TYPE: DNA
<213> ORGANISM: Artificial Sequence
<220> FEATURE:
<223> OTHER INFORMATION: Antisense Compound

<400> SEQUENCE: 15
agatatagat ag                                                    12

<210> SEQ ID NO 16
<211> LENGTH: 15
<212> TYPE: DNA
<213> ORGANISM: Artificial Sequence
<220> FEATURE:
<223> OTHER INFORMATION: Antisense Compound

<400> SEQUENCE: 16
atatagatat agata                                                 15

<210> SEQ ID NO 17
<211> LENGTH: 12
<212> TYPE: DNA
<213> ORGANISM: Artificial Sequence
<220> FEATURE:
<223> OTHER INFORMATION: Antisense Compound

<400> SEQUENCE: 17
tagatataga ta                                                    12

<210> SEQ ID NO 18
<211> LENGTH: 15
<212> TYPE: DNA
<213> ORGANISM: Artificial Sequence
<220> FEATURE:
<223> OTHER INFORMATION: Antisense Compound

<400> SEQUENCE: 18
tatatagata tagat                                                 15

<210> SEQ ID NO 19
<211> LENGTH: 12
<212> TYPE: DNA
<213> ORGANISM: Artificial Sequence
<220> FEATURE:
<223> OTHER INFORMATION: Antisense Compound

<400> SEQUENCE: 19
atagatatag at                                                    12

<210> SEQ ID NO 20
<211> LENGTH: 12
<212> TYPE: DNA
<213> ORGANISM: Artificial Sequence
<220> FEATURE:
<223> OTHER INFORMATION: Antisense Compound

<400> SEQUENCE: 20
tatagatata ga                                                    12

<210> SEQ ID NO 21
<211> LENGTH: 12
```

```
<212> TYPE: DNA
<213> ORGANISM: Artificial Sequence
<220> FEATURE:
<223> OTHER INFORMATION: Antisense Compound

<400> SEQUENCE: 21
atatagatat ag                                                    12

<210> SEQ ID NO 22
<211> LENGTH: 15
<212> TYPE: DNA
<213> ORGANISM: Artificial Sequence
<220> FEATURE:
<223> OTHER INFORMATION: Antisense Compound

<400> SEQUENCE: 22
atagctatat agata                                                 15

<210> SEQ ID NO 23
<211> LENGTH: 15
<212> TYPE: DNA
<213> ORGANISM: Artificial Sequence
<220> FEATURE:
<223> OTHER INFORMATION: Antisense Compound

<400> SEQUENCE: 23
aaaaaatagc tatat                                                 15

<210> SEQ ID NO 24
<211> LENGTH: 15
<212> TYPE: DNA
<213> ORGANISM: Artificial Sequence
<220> FEATURE:
<223> OTHER INFORMATION: Antisense Compound

<400> SEQUENCE: 24
gttaaaaaaa atagc                                                 15

<210> SEQ ID NO 25
<211> LENGTH: 15
<212> TYPE: DNA
<213> ORGANISM: Artificial Sequence
<220> FEATURE:
<223> OTHER INFORMATION: Antisense Compound

<400> SEQUENCE: 25
aggaagttaa aaaaa                                                 15

<210> SEQ ID NO 26
<211> LENGTH: 15
<212> TYPE: DNA
<213> ORGANISM: Artificial Sequence
<220> FEATURE:
<223> OTHER INFORMATION: Antisense Compound

<400> SEQUENCE: 26 aataaggaa gttaa                                                  15

<210> SEQ ID NO 27
<211> LENGTH: 15
<212> TYPE: DNA
<213> ORGANISM: Artificial Sequence
<220> FEATURE:
<223> OTHER INFORMATION: Antisense Compound

<400> SEQUENCE: 27
aggaaaataa aggaa                                                 15
```

```
<210> SEQ ID NO 28
<211> LENGTH: 15
<212> TYPE: DNA
<213> ORGANISM: Artificial Sequence
<220> FEATURE:
<223> OTHER INFORMATION: Antisense Compound

<400> SEQUENCE: 28
ctgtaaggaa aataa                                                          15

<210> SEQ ID NO 29
<211> LENGTH: 15
<212> TYPE: DNA
<213> ORGANISM: Artificial Sequence
<220> FEATURE:
<223> OTHER INFORMATION: Antisense Compound

<400> SEQUENCE: 29
attttgtcta aaacc                                                          15

<210> SEQ ID NO 30
<211> LENGTH: 15
<212> TYPE: DNA
<213> ORGANISM: Artificial Sequence
<220> FEATURE:
<223> OTHER INFORMATION: Antisense Compound

<400> SEQUENCE: 30
gattttgtct aaaac                                                          15

<210> SEQ ID NO 31
<211> LENGTH: 12
<212> TYPE: DNA
<213> ORGANISM: Artificial Sequence
<220> FEATURE:
<223> OTHER INFORMATION: Antisense Compound

<400> SEQUENCE: 31
ttttgtctaa aa                                                             12

<210> SEQ ID NO 32
<211> LENGTH: 15
<212> TYPE: DNA
<213> ORGANISM: Artificial Sequence
<220> FEATURE:
<223> OTHER INFORMATION: Antisense Compound

<400> SEQUENCE: 32
tgattttgtc taaaa                                                          15

<210> SEQ ID NO 33
<211> LENGTH: 12
<212> TYPE: DNA
<213> ORGANISM: Artificial Sequence
<220> FEATURE:
<223> OTHER INFORMATION: Antisense Compound

<400> SEQUENCE: 33
attttgtcta aa                                                             12

<210> SEQ ID NO 34
<211> LENGTH: 15
<212> TYPE: DNA
<213> ORGANISM: Artificial Sequence
<220> FEATURE:
<223> OTHER INFORMATION: Antisense Compound
```

```
<400> SEQUENCE: 34
ttgattttgt ctaaa                                          15

<210> SEQ ID NO 35
<211> LENGTH: 12
<212> TYPE: DNA
<213> ORGANISM: Artificial Sequence
<220> FEATURE:
<223> OTHER INFORMATION: Antisense Compound

<400> SEQUENCE: 35
gattttgtct aa                                             12

<210> SEQ ID NO 36
<211> LENGTH: 15
<212> TYPE: DNA
<213> ORGANISM: Artificial Sequence
<220> FEATURE:
<223> OTHER INFORMATION: Antisense Compound

<400> SEQUENCE: 36
tttgattttg tctaa                                          15

<210> SEQ ID NO 37
<211> LENGTH: 16
<212> TYPE: DNA
<213> ORGANISM: Artificial Sequence
<220> FEATURE:
<223> OTHER INFORMATION: Antisense Compound

<400> SEQUENCE: 37
ttttgatttt gtctaa                                         16

<210> SEQ ID NO 38
<211> LENGTH: 15
<212> TYPE: DNA
<213> ORGANISM: Artificial Sequence
<220> FEATURE:
<223> OTHER INFORMATION: Antisense Compound

<400> SEQUENCE: 38
ttttgatttt gtcta                                          15

<210> SEQ ID NO 39
<211> LENGTH: 12
<212> TYPE: DNA
<213> ORGANISM: Artificial Sequence
<220> FEATURE:
<223> OTHER INFORMATION: Antisense Compound

<400> SEQUENCE: 39
tgattttgtc ta                                             12

<210> SEQ ID NO 40
<211> LENGTH: 12
<212> TYPE: DNA
<213> ORGANISM: Artificial Sequence
<220> FEATURE:
<223> OTHER INFORMATION: Antisense Compound

<400> SEQUENCE: 40
ttgattttgt ct                                             12

<210> SEQ ID NO 41
<211> LENGTH: 15
```

```
<212> TYPE: DNA
<213> ORGANISM: Artificial Sequence
<220> FEATURE:
<223> OTHER INFORMATION: Antisense Compound

<400> SEQUENCE: 41
tttttgattt tgtct                                                   15

<210> SEQ ID NO 42
<211> LENGTH: 12
<212> TYPE: DNA
<213> ORGANISM: Artificial Sequence
<220> FEATURE:
<223> OTHER INFORMATION: Antisense Compound

<400> SEQUENCE: 42
tttgattttg tc                                                      12

<210> SEQ ID NO 43
<211> LENGTH: 15
<212> TYPE: DNA
<213> ORGANISM: Artificial Sequence
<220> FEATURE:
<223> OTHER INFORMATION: Antisense Compound

<400> SEQUENCE: 43 cttttgatt ttgtc                                                    15

<210> SEQ ID NO 44
<211> LENGTH: 12
<212> TYPE: DNA
<213> ORGANISM: Artificial Sequence
<220> FEATURE:
<223> OTHER INFORMATION: Antisense Compound

<400> SEQUENCE: 44
ttttgatttt gt                                                      12

<210> SEQ ID NO 45
<211> LENGTH: 12
<212> TYPE: DNA
<213> ORGANISM: Artificial Sequence
<220> FEATURE:
<223> OTHER INFORMATION: Antisense Compound

<400> SEQUENCE: 45
tttttgattt tg                                                      12

<210> SEQ ID NO 46
<211> LENGTH: 15
<212> TYPE: DNA
<213> ORGANISM: Artificial Sequence
<220> FEATURE:
<223> OTHER INFORMATION: Antisense Compound

<400> SEQUENCE: 46
cttctttttg atttt                                                   15

<210> SEQ ID NO 47
<211> LENGTH: 12
<212> TYPE: DNA
<213> ORGANISM: Artificial Sequence
<220> FEATURE:
<223> OTHER INFORMATION: Antisense Compound

<400> SEQUENCE: 47 cttttgatt tt                                                       12
```

<210> SEQ ID NO 48
<211> LENGTH: 12
<212> TYPE: DNA
<213> ORGANISM: Artificial Sequence
<220> FEATURE:
<223> OTHER INFORMATION: Antisense Compound

<400> SEQUENCE: 48 tcttttgat tt                                                        12

<210> SEQ ID NO 49
<211> LENGTH: 15
<212> TYPE: DNA
<213> ORGANISM: Artificial Sequence
<220> FEATURE:
<223> OTHER INFORMATION: Antisense Compound

<400> SEQUENCE: 49
ccttccttct ttttg                                                    15

<210> SEQ ID NO 50
<211> LENGTH: 15
<212> TYPE: DNA
<213> ORGANISM: Artificial Sequence
<220> FEATURE:
<223> OTHER INFORMATION: Antisense Compound

<400> SEQUENCE: 50
gagcaccttc cttct                                                    15

<210> SEQ ID NO 51
<211> LENGTH: 15
<212> TYPE: DNA
<213> ORGANISM: Artificial Sequence
<220> FEATURE:
<223> OTHER INFORMATION: Antisense Compound

<400> SEQUENCE: 51
aatgtgagca ccttc                                                    15

<210> SEQ ID NO 52
<211> LENGTH: 15
<212> TYPE: DNA
<213> ORGANISM: Artificial Sequence
<220> FEATURE:
<223> OTHER INFORMATION: Antisense Compound

<400> SEQUENCE: 52
taaggaatgt gagca                                                    15

<210> SEQ ID NO 53
<211> LENGTH: 18
<212> TYPE: DNA
<213> ORGANISM: Artificial Sequence
<220> FEATURE:
<223> OTHER INFORMATION: Antisense Compound

<400> SEQUENCE: 53
aatttaagga atgtgagc                                                 18

<210> SEQ ID NO 54
<211> LENGTH: 15
<212> TYPE: DNA
<213> ORGANISM: Artificial Sequence
<220> FEATURE:
<223> OTHER INFORMATION: Antisense Compound

```
<400> SEQUENCE: 54
ttaaggaatg tgagc                                                   15

<210> SEQ ID NO 55
<211> LENGTH: 18
<212> TYPE: DNA
<213> ORGANISM: Artificial Sequence
<220> FEATURE:
<223> OTHER INFORMATION: Antisense Compound

<400> SEQUENCE: 55
taatttaagg aatgtgag                                                18

<210> SEQ ID NO 56
<211> LENGTH: 15
<212> TYPE: DNA
<213> ORGANISM: Artificial Sequence
<220> FEATURE:
<223> OTHER INFORMATION: Antisense Compound

<400> SEQUENCE: 56
tttaaggaat gtgag                                                   15

<210> SEQ ID NO 57
<211> LENGTH: 12
<212> TYPE: DNA
<213> ORGANISM: Artificial Sequence
<220> FEATURE:
<223> OTHER INFORMATION: Antisense Compound

<400> SEQUENCE: 57
aaggaatgtg ag                                                      12

<210> SEQ ID NO 58
<211> LENGTH: 18
<212> TYPE: DNA
<213> ORGANISM: Artificial Sequence
<220> FEATURE:
<223> OTHER INFORMATION: Antisense Compound

<400> SEQUENCE: 58
ttaatttaag gaatgtga                                                18

<210> SEQ ID NO 59
<211> LENGTH: 15
<212> TYPE: DNA
<213> ORGANISM: Artificial Sequence
<220> FEATURE:
<223> OTHER INFORMATION: Antisense Compound

<400> SEQUENCE: 59
atttaaggaa tgtga                                                   15

<210> SEQ ID NO 60
<211> LENGTH: 12
<212> TYPE: DNA
<213> ORGANISM: Artificial Sequence
<220> FEATURE:
<223> OTHER INFORMATION: Antisense Compound

<400> SEQUENCE: 60
taaggaatgt ga                                                      12

<210> SEQ ID NO 61
<211> LENGTH: 18
```

```
<212> TYPE: DNA
<213> ORGANISM: Artificial Sequence
<220> FEATURE:
<223> OTHER INFORMATION: Antisense Compound

<400> SEQUENCE: 61
cttaatttaa ggaatgtg                                           18

<210> SEQ ID NO 62
<211> LENGTH: 15
<212> TYPE: DNA
<213> ORGANISM: Artificial Sequence
<220> FEATURE:
<223> OTHER INFORMATION: Antisense Compound

<400> SEQUENCE: 62
aatttaagga atgtg                                              15

<210> SEQ ID NO 63
<211> LENGTH: 12
<212> TYPE: DNA
<213> ORGANISM: Artificial Sequence
<220> FEATURE:
<223> OTHER INFORMATION: Antisense Compound

<400> SEQUENCE: 63
ttaaggaatg tg                                                 12

<210> SEQ ID NO 64
<211> LENGTH: 15
<212> TYPE: DNA
<213> ORGANISM: Artificial Sequence
<220> FEATURE:
<223> OTHER INFORMATION: Antisense Compound

<400> SEQUENCE: 64
taatttaagg aatgt                                              15

<210> SEQ ID NO 65
<211> LENGTH: 18
<212> TYPE: DNA
<213> ORGANISM: Artificial Sequence
<220> FEATURE:
<223> OTHER INFORMATION: Antisense Compound

<400> SEQUENCE: 65
ccttaattta aggaatgt                                           18

<210> SEQ ID NO 66
<211> LENGTH: 12
<212> TYPE: DNA
<213> ORGANISM: Artificial Sequence
<220> FEATURE:
<223> OTHER INFORMATION: Antisense Compound

<400> SEQUENCE: 66
tttaaggaat gt                                                 12

<210> SEQ ID NO 67
<211> LENGTH: 15
<212> TYPE: DNA
<213> ORGANISM: Artificial Sequence
<220> FEATURE:
<223> OTHER INFORMATION: Antisense Compound

<400> SEQUENCE: 67
ttaatttaag gaatg                                              15
```

```
<210> SEQ ID NO 68
<211> LENGTH: 12
<212> TYPE: DNA
<213> ORGANISM: Artificial Sequence
<220> FEATURE:
<223> OTHER INFORMATION: Antisense Compound

<400> SEQUENCE: 68
atttaaggaa tg                                                             12

<210> SEQ ID NO 69
<211> LENGTH: 15
<212> TYPE: DNA
<213> ORGANISM: Artificial Sequence
<220> FEATURE:
<223> OTHER INFORMATION: Antisense Compound

<400> SEQUENCE: 69
cttaatttaa ggaat                                                          15

<210> SEQ ID NO 70
<211> LENGTH: 12
<212> TYPE: DNA
<213> ORGANISM: Artificial Sequence
<220> FEATURE:
<223> OTHER INFORMATION: Antisense Compound

<400> SEQUENCE: 70
aatttaagga at                                                             12

<210> SEQ ID NO 71
<211> LENGTH: 15
<212> TYPE: DNA
<213> ORGANISM: Artificial Sequence
<220> FEATURE:
<223> OTHER INFORMATION: Antisense Compound

<400> SEQUENCE: 71
ccttaattta aggaa                                                          15

<210> SEQ ID NO 72
<211> LENGTH: 12
<212> TYPE: DNA
<213> ORGANISM: Artificial Sequence
<220> FEATURE:
<223> OTHER INFORMATION: Antisense Compound

<400> SEQUENCE: 72
taatttaagg aa                                                             12

<210> SEQ ID NO 73
<211> LENGTH: 15
<212> TYPE: DNA
<213> ORGANISM: Artificial Sequence
<220> FEATURE:
<223> OTHER INFORMATION: Antisense Compound

<400> SEQUENCE: 73
tccttaattt aagga                                                          15

<210> SEQ ID NO 74
<211> LENGTH: 12
<212> TYPE: DNA
<213> ORGANISM: Artificial Sequence
<220> FEATURE:
<223> OTHER INFORMATION: Antisense Compound
```

```
<400> SEQUENCE: 74
ttaatttaag ga                                                         12

<210> SEQ ID NO 75
<211> LENGTH: 12
<212> TYPE: DNA
<213> ORGANISM: Artificial Sequence
<220> FEATURE:
<223> OTHER INFORMATION: Antisense Compound

<400> SEQUENCE: 75
cttaatttaa gg                                                         12

<210> SEQ ID NO 76
<211> LENGTH: 12
<212> TYPE: DNA
<213> ORGANISM: Artificial Sequence
<220> FEATURE:
<223> OTHER INFORMATION: Antisense Compound

<400> SEQUENCE: 76
ccttaattta ag                                                         12

<210> SEQ ID NO 77
<211> LENGTH: 15
<212> TYPE: DNA
<213> ORGANISM: Artificial Sequence
<220> FEATURE:
<223> OTHER INFORMATION: Antisense Compound

<400> SEQUENCE: 77
tgctggcaga cttac                                                      15

<210> SEQ ID NO 78
<211> LENGTH: 15
<212> TYPE: DNA
<213> ORGANISM: Artificial Sequence
<220> FEATURE:
<223> OTHER INFORMATION: Antisense Compound

<400> SEQUENCE: 78
cataatgctg gcaga                                                      15

<210> SEQ ID NO 79
<211> LENGTH: 15
<212> TYPE: DNA
<213> ORGANISM: Artificial Sequence
<220> FEATURE:
<223> OTHER INFORMATION: Antisense Compound

<400> SEQUENCE: 79
tcataatgct ggcag                                                      15

<210> SEQ ID NO 80
<211> LENGTH: 15
<212> TYPE: DNA
<213> ORGANISM: Artificial Sequence
<220> FEATURE:
<223> OTHER INFORMATION: Antisense Compound

<400> SEQUENCE: 80
ttcataatgc tggca                                                      15

<210> SEQ ID NO 81
<211> LENGTH: 15
```

```
<212> TYPE: DNA
<213> ORGANISM: Artificial Sequence
<220> FEATURE:
<223> OTHER INFORMATION: Antisense Compound

<400> SEQUENCE: 81
tttcataatg ctggc                                                    15

<210> SEQ ID NO 82
<211> LENGTH: 20
<212> TYPE: DNA
<213> ORGANISM: Artificial Sequence
<220> FEATURE:
<223> OTHER INFORMATION: Antisense Compound

<400> SEQUENCE: 82
attcactttc ataatgctgg                                               20

<210> SEQ ID NO 83
<211> LENGTH: 15
<212> TYPE: DNA
<213> ORGANISM: Artificial Sequence
<220> FEATURE:
<223> OTHER INFORMATION: Antisense Compound

<400> SEQUENCE: 83
ctttcataat gctgg                                                    15

<210> SEQ ID NO 84
<211> LENGTH: 12
<212> TYPE: DNA
<213> ORGANISM: Artificial Sequence
<220> FEATURE:
<223> OTHER INFORMATION: Antisense Compound

<400> SEQUENCE: 84
tcataatgct gg                                                       12

<210> SEQ ID NO 85
<211> LENGTH: 15
<212> TYPE: DNA
<213> ORGANISM: Artificial Sequence
<220> FEATURE:
<223> OTHER INFORMATION: Antisense Compound

<400> SEQUENCE: 85
actttcataa tgctg                                                    15

<210> SEQ ID NO 86
<211> LENGTH: 12
<212> TYPE: DNA
<213> ORGANISM: Artificial Sequence
<220> FEATURE:
<223> OTHER INFORMATION: Antisense Compound

<400> SEQUENCE: 86
ttcataatgc tg                                                       12

<210> SEQ ID NO 87
<211> LENGTH: 15
<212> TYPE: DNA
<213> ORGANISM: Artificial Sequence
<220> FEATURE:
<223> OTHER INFORMATION: Antisense Compound

<400> SEQUENCE: 87
cactttcata atgct                                                    15
```

-continued

```
<210> SEQ ID NO 88
<211> LENGTH: 12
<212> TYPE: DNA
<213> ORGANISM: Artificial Sequence
<220> FEATURE:
<223> OTHER INFORMATION: Antisense Compound

<400> SEQUENCE: 88
tttcataatg ct                                                          12

<210> SEQ ID NO 89
<211> LENGTH: 15
<212> TYPE: DNA
<213> ORGANISM: Artificial Sequence
<220> FEATURE:
<223> OTHER INFORMATION: Antisense Compound

<400> SEQUENCE: 89
tcactttcat aatgc                                                       15

<210> SEQ ID NO 90
<211> LENGTH: 12
<212> TYPE: DNA
<213> ORGANISM: Artificial Sequence
<220> FEATURE:
<223> OTHER INFORMATION: Antisense Compound

<400> SEQUENCE: 90
ctttcataat gc                                                          12

<210> SEQ ID NO 91
<211> LENGTH: 15
<212> TYPE: DNA
<213> ORGANISM: Artificial Sequence
<220> FEATURE:
<223> OTHER INFORMATION: Antisense Compound

<400> SEQUENCE: 91
ttcactttca taatg                                                       15

<210> SEQ ID NO 92
<211> LENGTH: 12
<212> TYPE: DNA
<213> ORGANISM: Artificial Sequence
<220> FEATURE:
<223> OTHER INFORMATION: Antisense Compound

<400> SEQUENCE: 92
actttcataa tg                                                          12

<210> SEQ ID NO 93
<211> LENGTH: 15
<212> TYPE: DNA
<213> ORGANISM: Artificial Sequence
<220> FEATURE:
<223> OTHER INFORMATION: Antisense Compound

<400> SEQUENCE: 93
attcactttc ataat                                                       15

<210> SEQ ID NO 94
<211> LENGTH: 12
<212> TYPE: DNA
<213> ORGANISM: Artificial Sequence
<220> FEATURE:
<223> OTHER INFORMATION: Antisense Compound
```

```
<400> SEQUENCE: 94
cactttcata at                                          12

<210> SEQ ID NO 95
<211> LENGTH: 15
<212> TYPE: DNA
<213> ORGANISM: Artificial Sequence
<220> FEATURE:
<223> OTHER INFORMATION: Antisense Compound

<400> SEQUENCE: 95
gattcacttt cataa                                       15

<210> SEQ ID NO 96
<211> LENGTH: 12
<212> TYPE: DNA
<213> ORGANISM: Artificial Sequence
<220> FEATURE:
<223> OTHER INFORMATION: Antisense Compound

<400> SEQUENCE: 96
tcactttcat aa                                          12

<210> SEQ ID NO 97
<211> LENGTH: 12
<212> TYPE: DNA
<213> ORGANISM: Artificial Sequence
<220> FEATURE:
<223> OTHER INFORMATION: Antisense Compound

<400> SEQUENCE: 97
ttcactttca ta                                          12

<210> SEQ ID NO 98
<211> LENGTH: 12
<212> TYPE: DNA
<213> ORGANISM: Artificial Sequence
<220> FEATURE:
<223> OTHER INFORMATION: Antisense Compound

<400> SEQUENCE: 98
attcactttc at                                          12

<210> SEQ ID NO 99
<211> LENGTH: 15
<212> TYPE: DNA
<213> ORGANISM: Artificial Sequence
<220> FEATURE:
<223> OTHER INFORMATION: Antisense Compound

<400> SEQUENCE: 99
agtaagattc acttt                                       15

<210> SEQ ID NO 100
<211> LENGTH: 15
<212> TYPE: DNA
<213> ORGANISM: Artificial Sequence
<220> FEATURE:
<223> OTHER INFORMATION: Antisense Compound

<400> SEQUENCE: 100
acaaaagtaa gattc                                       15

<210> SEQ ID NO 101
<211> LENGTH: 15
```

```
<212> TYPE: DNA
<213> ORGANISM: Artificial Sequence
<220> FEATURE:
<223> OTHER INFORMATION: Antisense Compound

<400> SEQUENCE: 101
gttttacaaa agtaa                                                        15

<210> SEQ ID NO 102
<211> LENGTH: 15
<212> TYPE: DNA
<213> ORGANISM: Artificial Sequence
<220> FEATURE:
<223> OTHER INFORMATION: Antisense Compound

<400> SEQUENCE: 102
ataaagtttt acaaa                                                        15

<210> SEQ ID NO 103
<211> LENGTH: 15
<212> TYPE: DNA
<213> ORGANISM: Artificial Sequence
<220> FEATURE:
<223> OTHER INFORMATION: Antisense Compound

<400> SEQUENCE: 103
aaaccataaa gtttt                                                        15

<210> SEQ ID NO 104
<211> LENGTH: 15
<212> TYPE: DNA
<213> ORGANISM: Artificial Sequence
<220> FEATURE:
<223> OTHER INFORMATION: Antisense Compound

<400> SEQUENCE: 104
tccacaaacc ataaa                                                        15

<210> SEQ ID NO 105
<211> LENGTH: 10
<212> TYPE: DNA
<213> ORGANISM: Artificial Sequence
<220> FEATURE:
<223> OTHER INFORMATION: Consensus splice site

<400> SEQUENCE: 105
gtaagtactt                                                              10

<210> SEQ ID NO 106
<211> LENGTH: 37
<212> TYPE: DNA
<213> ORGANISM: Artificial Sequence
<220> FEATURE:
<223> OTHER INFORMATION: Primer

<400> SEQUENCE: 106
agataaaagg ttaatctaga tccctactag aattctc                                37

<210> SEQ ID NO 107
<211> LENGTH: 37
<212> TYPE: DNA
<213> ORGANISM: Artificial Sequence
<220> FEATURE:
<223> OTHER INFORMATION: Primer

<400> SEQUENCE: 107
gagaattcta gtagggatct agattaacct tttatct                                37
```

<210> SEQ ID NO 108
<211> LENGTH: 24
<212> TYPE: DNA
<213> ORGANISM: Artificial Sequence
<220> FEATURE:
<223> OTHER INFORMATION: Primer

<400> SEQUENCE: 108
aattgctaac gcagtcagtg cttc                                              24

<210> SEQ ID NO 109
<211> LENGTH: 33
<212> TYPE: DNA
<213> ORGANISM: Artificial Sequence
<220> FEATURE:
<223> OTHER INFORMATION: Primer

<400> SEQUENCE: 109
aatatgatca gcaaaacaaa gtcacataac tac                                    33

<210> SEQ ID NO 110
<211> LENGTH: 42
<212> TYPE: DNA
<213> ORGANISM: Artificial Sequence
<220> FEATURE:
<223> OTHER INFORMATION: Primer

<400> SEQUENCE: 110
gtgactttgt tttgctgatc atattttgtt gaataaaata ag                          42

<210> SEQ ID NO 111
<211> LENGTH: 24
<212> TYPE: DNA
<213> ORGANISM: Artificial Sequence
<220> FEATURE:
<223> OTHER INFORMATION: Primer

<400> SEQUENCE: 111
aatgtatctt atcatgtctg ctcg                                              24

<210> SEQ ID NO 112
<211> LENGTH: 24
<212> TYPE: DNA
<213> ORGANISM: Artificial Sequence
<220> FEATURE:
<223> OTHER INFORMATION: Primer

<400> SEQUENCE: 112
aatgtatctt atcatgtctg ctcg                                              24

<210> SEQ ID NO 113
<211> LENGTH: 38
<212> TYPE: DNA
<213> ORGANISM: Artificial Sequence
<220> FEATURE:
<223> OTHER INFORMATION: Primer

<400> SEQUENCE: 113
aagtacttac ctgtaacgct tcacattcca gatctgtc                               38

<210> SEQ ID NO 114
<211> LENGTH: 15
<212> TYPE: DNA

```
<213> ORGANISM: Artificial Sequence
<220> FEATURE:
<223> OTHER INFORMATION: Antisense Compound

<400> SEQUENCE: 114
ttgtattcta tgttt                                                    15
```